(12) United States Patent
Chandrasekhar

(10) Patent No.: US 9,594,284 B2
(45) Date of Patent: Mar. 14, 2017

(54) COMPLIMENTARY POLYMER ELECTROCHROMIC DEVICE

(71) Applicant: Ashwin-Ushas Corporation, Inc., Holmdel, NJ (US)

(72) Inventor: Prasanna Chandrasekhar, Holmdel, NJ (US)

(73) Assignee: Ashwin-Ushas Corporation, Inc., Holmdel, NJ (US)

( * ) Notice: Subject to any disclaimer, the term of this patent is extended or adjusted under 35 U.S.C. 154(b) by 0 days.

(21) Appl. No.: 14/738,036

(22) Filed: Jun. 12, 2015

(65) Prior Publication Data

US 2015/0275385 A1  Oct. 1, 2015

Related U.S. Application Data

(62) Division of application No. 13/677,197, filed on Nov. 14, 2012, now Pat. No. 9,274,395.

(60) Provisional application No. 61/560,243, filed on Nov. 15, 2011.

(51) Int. Cl.

| | | |
|---|---|---|
| *C07C 211/55* | (2006.01) | |
| *G02F 1/15* | (2006.01) | |
| *B05D 5/12* | (2006.01) | |
| *C07D 495/04* | (2006.01) | |
| *C07C 57/38* | (2006.01) | |
| *C07C 29/147* | (2006.01) | |
| *C07C 33/46* | (2006.01) | |
| *C07C 69/65* | (2006.01) | |
| *C09K 9/02* | (2006.01) | |
| *C25D 9/02* | (2006.01) | |
| *G02F 1/1343* | (2006.01) | |
| *G02F 1/155* | (2006.01) | |

(52) U.S. Cl.
CPC ............. *G02F 1/1506* (2013.01); *B05D 5/12* (2013.01); *C07C 29/147* (2013.01); *C07C 33/46* (2013.01); *C07C 57/38* (2013.01); *C07C 69/65* (2013.01); *C07D 495/04* (2013.01); *C09K 9/02* (2013.01); *C25D 9/02* (2013.01); *G02F 1/13439* (2013.01); *G02F 1/155* (2013.01); *C09K 2211/1433* (2013.01); *C09K 2211/1491* (2013.01); *G02F 2001/1502* (2013.01); *G02F 2001/1515* (2013.01)

(58) Field of Classification Search
None
See application file for complete search history.

(56) References Cited

U.S. PATENT DOCUMENTS

| | | | |
|---|---|---|---|
| 3,807,832 A | 4/1974 | Castellion | |
| 3,844,636 A | 10/1974 | Maricle | |
| 4,215,917 A | 8/1980 | Giglia | |
| 4,272,163 A | 6/1981 | Samokhin | |
| 4,304,465 A | 12/1981 | Diaz | |
| 4,500,840 A | 2/1985 | Galwey | |
| 4,529,873 A | 7/1985 | Ballmer | |
| 4,559,122 A | 12/1985 | Folco | |
| 4,586,792 A | 5/1986 | Yang | |
| 4,618,218 A | 10/1986 | Shaw | |
| 4,749,260 A | 6/1988 | Yang | |
| 4,874,481 A | 10/1989 | Suzuki | |
| 4,886,572 A * | 12/1989 | Kimura | H01M 4/137 204/242 |
| 4,902,108 A | 2/1990 | Byker | |
| 4,939,043 A | 7/1990 | Biricik | |
| 5,079,334 A | 1/1992 | Epstein | |
| 5,095,153 A | 3/1992 | Agnes | |
| 5,124,080 A | 6/1992 | Shabrang | |
| 5,137,991 A | 8/1992 | Epstein | |
| 5,159,031 A | 10/1992 | Epstein | |
| 5,164,465 A | 11/1992 | Epstein | |
| 5,173,443 A | 12/1992 | Biricik | |
| 5,184,156 A | 2/1993 | Black | |
| 5,241,411 A | 8/1993 | Arribart | |
| 5,253,100 A | 10/1993 | Yang | |
| 5,373,305 A | 12/1994 | Lepore, Jr. | |
| 5,373,306 A | 12/1994 | Amore | |
| 5,413,739 A | 5/1995 | Coleman | |
| 5,441,629 A | 8/1995 | Kosaki | |
| 5,446,576 A | 8/1995 | Lynam | |
| 5,446,577 A | 8/1995 | Bennett | |
| 5,455,637 A | 10/1995 | Kallman | |
| 5,455,638 A | 10/1995 | Kallman | |
| 5,466,356 A | 11/1995 | Schneider | |
| 5,500,759 A | 3/1996 | Coleman | |
| 5,561,206 A | 10/1996 | Yamamoto | |
| 5,578,191 A | 11/1996 | Robert | |
| 5,608,567 A | 3/1997 | Grupp | |

(Continued)

FOREIGN PATENT DOCUMENTS

| | | |
|---|---|---|
| CN | 101939399 A | 1/2011 |
| CN | 102176102 | 9/2011 |

(Continued)

OTHER PUBLICATIONS

Autolab Application Note EC08, "Basic overview of the working principle of a potentiostat/galvanostat (PGSTAT)—Electrochemical cell setup," Dec. 20, 2011.
International Search Report and Written Opinion dated Jan. 30, 2015 for PCT Appln No. PCT/US2014/065170.
(Non-edited textbook): Chandrasekhar, P. Conducting Polymers: Fundamentals and Applications. A Practical Approach, with foreword by Lawrence Dalton: Kluwer Academic Publishers (now Springer Verlag), Dordrecht, The Netherlands and Norwell, MA, USAM ISBN No. 0-7923-8564-0 (Aug. 1999).

(Continued)

*Primary Examiner* — Noble Jarrell
(74) *Attorney, Agent, or Firm* — Morgan Lewis & Bockius LLP

(57) ABSTRACT

A complimentary polymer or "dual-polymer" electrochromic device and methods of preparing the same are provided.

11 Claims, 18 Drawing Sheets

(56) References Cited

U.S. PATENT DOCUMENTS

| | | |
|---|---|---|
| 5,657,150 A | 8/1997 | Kallman |
| 5,728,943 A | 3/1998 | Colter, Jr. |
| 5,835,185 A | 11/1998 | Kallman |
| 5,864,419 A | 1/1999 | Lynam |
| 5,900,720 A | 5/1999 | Kallman |
| 5,951,844 A | 9/1999 | Jansen |
| 5,969,847 A | 10/1999 | Coleman |
| 5,973,818 A | 10/1999 | Sjursen |
| 5,995,273 A | 11/1999 | Chandrasekhar |
| 6,033,592 A | 3/2000 | Chandrasekhar |
| 6,063,253 A | 5/2000 | Shreve |
| 6,083,376 A | 7/2000 | Akram |
| 6,089,721 A | 7/2000 | Schierbeek |
| 6,099,117 A | 8/2000 | Gregory |
| 6,130,772 A | 10/2000 | Cava |
| 6,132,583 A | 10/2000 | Stone |
| 6,189,835 B1 | 2/2001 | Kaufman |
| 6,261,425 B1 | 7/2001 | Huang |
| 6,267,853 B1 | 7/2001 | Dordi |
| 6,270,647 B1 | 8/2001 | Graham |
| 6,279,857 B1 | 8/2001 | Roth |
| 6,294,060 B1 | 9/2001 | Webb |
| 6,299,751 B1 | 10/2001 | Kaufman |
| 6,299,753 B1 | 10/2001 | Chao |
| 6,327,069 B1 | 12/2001 | Allemand |
| 6,339,334 B1 | 1/2002 | Park |
| 6,402,924 B1 | 6/2002 | Martin |
| 6,409,903 B1 | 6/2002 | Chung |
| 6,428,684 B1 | 8/2002 | Warburton |
| 6,538,796 B1 | 3/2003 | Swanson |
| 6,547,945 B2 | 4/2003 | Shallow |
| 6,551,484 B2 | 4/2003 | Hey |
| 6,607,652 B2 | 8/2003 | Webb |
| 6,620,304 B1 | 9/2003 | Hoffacker |
| 6,687,631 B2 | 2/2004 | Yoon |
| 6,713,774 B2 | 3/2004 | DeSteese |
| 6,733,909 B2 | 5/2004 | Ding |
| 6,818,110 B1 | 11/2004 | Warren |
| 6,837,978 B1 | 1/2005 | Hey |
| 6,859,297 B2 | 2/2005 | Lee |
| 7,033,466 B2 | 4/2006 | Riewe |
| 7,156,965 B1 | 1/2007 | Li |
| 7,180,649 B2 | 2/2007 | Morrison |
| 7,219,860 B2 | 5/2007 | Wehner |
| 7,223,323 B2 | 5/2007 | Yang |
| 7,229,545 B2 | 6/2007 | Sewing |
| 7,247,222 B2 | 7/2007 | Yang |
| 7,270,891 B2 | 9/2007 | Roth |
| 7,277,215 B2 | 10/2007 | Greer |
| 7,306,332 B2 | 12/2007 | Chen |
| 7,333,258 B2 | 2/2008 | Yang |
| 7,342,708 B2 | 3/2008 | Ho |
| RE40,218 E | 4/2008 | Landau |
| 7,355,161 B2 | 4/2008 | Romig |
| 7,374,283 B2 | 5/2008 | Blum |
| 7,384,522 B2 | 6/2008 | Marszal |
| 7,390,123 B2 | 6/2008 | Friedman |
| 7,427,338 B2 | 9/2008 | Dordi |
| 7,427,346 B2 | 9/2008 | Tom |
| 7,449,098 B1 | 11/2008 | Mayer |
| 7,500,747 B2 | 3/2009 | Howell |
| 7,578,912 B2 | 8/2009 | Buehler |
| 7,675,667 B2 | 3/2010 | Xu |
| 7,686,938 B2 | 3/2010 | Gill |
| 7,691,284 B2 | 4/2010 | Cumberland |
| 7,704,352 B2 | 4/2010 | Lopatin |
| 7,733,335 B2 | 6/2010 | Zehner |
| 7,738,155 B2 | 6/2010 | Agrawal |
| 7,761,053 B2 | 7/2010 | Kruzelecky |
| 7,828,944 B2 | 11/2010 | Nagashima |
| 7,874,666 B2 | 1/2011 | Xu |
| 7,940,062 B1 | 5/2011 | Miller |
| 7,951,902 B2 | 5/2011 | Sotzing |
| 7,952,557 B2 | 5/2011 | Amundson |
| 7,954,942 B2 | 6/2011 | Calilung |
| 7,999,992 B2 | 8/2011 | Mazurkiewicz |
| 8,005,526 B2 | 8/2011 | Martin |
| 8,016,415 B2 | 9/2011 | Figler |
| 8,017,217 B1 | 9/2011 | Gregoire |
| 8,018,644 B2 | 9/2011 | Gustavsson |
| 8,109,629 B2 | 2/2012 | Howell |
| 8,133,369 B2 | 3/2012 | Tam |
| 8,234,507 B2 | 7/2012 | Zhu |
| 8,241,228 B1 | 8/2012 | Cohen |
| 8,337,014 B2 | 12/2012 | Kokonaski |
| 8,408,699 B2 | 4/2013 | Blum |
| 8,434,863 B2 | 5/2013 | Howell |
| 8,465,151 B2 | 6/2013 | Howell |
| 8,496,790 B2 | 7/2013 | Wilson |
| 8,500,983 B2 | 8/2013 | Ponnuswamy |
| 8,541,174 B2 | 9/2013 | Wohlstadter |
| 8,551,315 B2 | 10/2013 | Cohen |
| 8,603,316 B2 | 12/2013 | Cohen |
| 8,657,438 B2 | 2/2014 | Jacobs |
| 8,708,483 B2 | 4/2014 | Kokonaski |
| 8,741,590 B2 | 6/2014 | Heller |
| 8,758,591 B2 | 6/2014 | Adeloju |
| 8,783,864 B2 | 7/2014 | Matsui |
| 8,902,486 B1 | 12/2014 | Chandrasekhar |
| 8,931,896 B2 | 1/2015 | Blum |
| 8,932,443 B2 | 1/2015 | Sto.Domingo |
| 8,944,590 B2 | 2/2015 | Blum |
| 9,018,019 B2 | 4/2015 | Parker |
| 9,018,802 B2 | 4/2015 | Sun |
| 2002/0157959 A1 | 10/2002 | Kronenberg |
| 2002/0191270 A1 | 12/2002 | Lu |
| 2003/0202249 A1 | 10/2003 | Schierbeek |
| 2003/0214695 A1 | 11/2003 | Abramson |
| 2003/0227663 A1 | 12/2003 | Agrawal |
| 2004/0256222 A1 | 12/2004 | Griego |
| 2006/0070883 A1 | 4/2006 | Bejan |
| 2007/0008603 A1 | 1/2007 | Sotzing |
| 2007/0103761 A1 | 5/2007 | Giron |
| 2007/0215457 A1 | 9/2007 | Glassman |
| 2008/0131773 A1 | 6/2008 | Lucas |
| 2008/0245471 A1 | 10/2008 | Goad |
| 2009/0067030 A1 | 3/2009 | Liu |
| 2009/0096745 A1 | 4/2009 | Sprague |
| 2009/0114537 A1 | 5/2009 | Bourgerette |
| 2009/0203873 A1 | 8/2009 | Sotzing |
| 2010/0253603 A1 | 10/2010 | Righi |
| 2010/0280561 A1 | 11/2010 | Song |
| 2011/0111147 A1 | 5/2011 | Agrawal |
| 2011/0135837 A1 | 6/2011 | Burdis |
| 2011/0151317 A1 | 6/2011 | Giroud |
| 2011/0164303 A1 | 7/2011 | Hampp |
| 2011/0187684 A1 | 8/2011 | Amundson |
| 2011/0255142 A1 | 10/2011 | Ash |
| 2012/0205258 A1 | 8/2012 | Noble |
| 2012/0235900 A1 | 9/2012 | Border |
| 2013/0120821 A1 | 5/2013 | Chandrasekhar |
| 2013/0161600 A1 | 6/2013 | Sotzing |
| 2013/0235323 A1 | 9/2013 | Sotzing |
| 2013/0278989 A1 | 10/2013 | Lam |
| 2014/0097088 A1 | 4/2014 | Stowell |
| 2014/0268283 A1 | 9/2014 | Chandrasekhar |
| 2014/0284216 A1 | 9/2014 | MacNeil |

FOREIGN PATENT DOCUMENTS

| | | |
|---|---|---|
| CN | 202705536 | 1/2013 |
| CN | 203256361 | 10/2013 |
| CN | 103436946 | 12/2013 |
| CN | 103498134 | 1/2014 |
| CN | 203530467 | 4/2014 |
| EP | 0915189 | 5/1999 |
| EP | 0989209 | 3/2000 |
| EP | 1533400 | 5/2005 |
| EP | 2049943 | 4/2009 |
| WO | 9314436 | 7/1993 |
| WO | 9728484 | 8/1997 |
| WO | 9837453 | 8/1998 |
| WO | 9845504 | 10/1998 |
| WO | 0204715 | 1/2002 |

(56) References Cited

FOREIGN PATENT DOCUMENTS

| WO | 02082172 | 10/2002 |
|----|----------|---------|
| WO | 2004001100 | 12/2003 |
| WO | 2005050294 | 6/2005 |
| WO | 2007146862 | 12/2007 |
| WO | 2009067030 | 3/2009 |
| WO | 2009058877 | 5/2009 |
| WO | 2009114965 | 9/2009 |
| WO | 2012158966 | 11/2012 |
| WO | 2015014292 | 2/2015 |

OTHER PUBLICATIONS

A. Masulaitis, et al., "Use of novel dopants and doping effects for broadband signature control in conducting polymer systems," The International Society for Optical Engineering, 2528:190-197 (1995).
Chandrasekhar, P., et al., "High Performance Variable Emittance Devices for Spacecraft Application Based on Conducting Polymers Coupled with Ionic Liquids," AIP Conf. Proc. (2009) 1103:101-104.
Chandrasekhar, P., et al., "Large, Switchable Electrochromism in the Visible Through Far-Infrared in Conducting Polymer Devices," Adv. Funct. Mater. (2002) 12:95-103.
Chandrasekhar, P., Masulaitis, A.M.; Gumbs, R.W., "Novel Synthesis, Spectroelectrochemical, Electrochemical and Chronovoltabsorptometric Characterization of Poly(Isothianaphthene)" Synth. Met., (1990), 36(3), 303-326.
Chandrasekhar, P.; Gumbs, R.W., Novel Synthesis, Spectroelectrochemical, Electrochemical and Chronovoltabsorptometric Characterization of Family of Poly-(Aromatic Amines), Novel Processible Conducting Polymers. I. Poly(benzidines)', J. Electrochem. Soc., (1991), 138, 1337-1346.
Chandrasekhar, P.; Thorne, J.R.G., Hochstrasser, R.M., Third-order Nonlinear Optical Properties of Poly(diphenyl Amine) and Poly(4-Amino Biphenyl), Novel Processible Conducting Polymers', Appl. Phys. Lett., (1991), 59, 1661-3.
Chandrasekhar, P.; Wheeler, R.A.; Hoffmann, Roald, "Sigma Bond Cleavage in Coordinated Dioxygen: The Case of the u-Peroxo Complex [(THF)3Cl2V(III)(O22)-V(III)CL2(THF)3] and Vanadyl Formation in Solution", Inorg. Chim. Acta, (1987), 129:51-59.
Fillion, E.; Fishlock, D.; Wilsily, A.; Goll, J. M., "Meldrum's Acids as Acylating Agents in the Catylitic Intramolecular Friedel-Crafts Reaction," J. Org. Chem. 2005, 70, 1316.
Gazotti, W.A.; Casalbore-Miceli, G.; Geri, A.; De Paoli, M.-A., "A Solid-State Electrochromic Device Based on Two Optically Complementary Conducting Polymers", Adv. Mat. 10, 60-64 (1998).
Groenendaal, L.; Jonas, F.; Freitag, D.; Pielartzik, H.; Reynolds, J.R., "Poly(3,4-ethylenedioxythiophene) and Its Deriatives: Past, Present and Future", Adv. Mat., 12, 481-494 (2000).
Guay, J.; Dao, L.H., "Formation of poly(4-phenylaniline) by electropolymerization of 4-aminobiphenyl or diphenylamine", J. Electroanal. Chem., 274, 135-142 (1989).
Guay, J.; Leclerc, M.; Dao, L.H., "Conducting polymer derived from 4- aminobiphenyl" J. Electroanal. Chem. Interfac. Electrochem., 251, 31-39 (1988).
Hotta, S.; Rughooputh, S.D.D.V.; Heeger, A.J.; Wudl, F., "Spectroscopic Studies of Soluble Poly(3-alkylthienylenes," Macromolecules, 20, 212 (1987).
Hsu, C-Y.; Lee, K-M.; Huang, J-H.; Justin Thomas, K.R.; Lin, J.T.; Ho, K-C., "A novel photoelectrochromic device with dual application based on poly(3,4-alkylenedioxytiophene) thin film and an organic dye", Journal of Power Sources, 185, 1505-1508 (2008).
International Search Report and Written Opinion dated Mar. 29, 2013 for PCT Appln No. PCT/US2012/065123.
Ivernale, M.A.; Seshadri, V.; Mamangun, D.M.D.; Ding, Y.; Filloramo, J; and Sotzing, G.A., "Polythieno[3,4-b]thiophene as an Optically Transparent Ion-Storage Layer," Chem. Mater. 2009, 21, 3332-3336.

Krishnamoorthy, K.; Ambade, A.V.; Kanungo, M.; Contractor, A.Q.; Kumar, A., "Rational design of an electorchromic polymer with high contrast in the visible region: dibenzyl substituted poly(3,4-propylenedioxythiohene)", J. Mat. Chem. 11, 2909-2911 (2001).
Leclerc, M.; Guay, J.; Dao, L.H., "Synthesis and properties of electrochromic polymers from toluidines", J. Electroanal. Chem. Interfac. Electrochem., 251, 21-29 (1988).
Lu, W., et al., "Use of Ionic Liquids for A-Conjugated Polymer Electrochemical Devices," Science (2002) 297:983-986.
Menon, R.; Yoon, C.O.; Moses, D; Heeger, A.J., "Metal-Insulator Transition in Doped Conducting Polymers", in Handbook of Conducting Polymers, 2nd Edition, p. 27, Ed by Skotheim, T.A.; Reynolds, J. (Eds.), CRC Press, Boca Rato, FL, USA, (1998).
Nguyen, M.T.; Dao, L.H., "Electrochemical, electrochromic, and conductive properties of poly(N-alkyldiphenylamine) polymers", J. Chem. Soc., Chem. Commun., 1221-1222 (1990).
Nguyen, M.T.; Dao, L.H., "Synthesis, characterization and properties of poly-(3-methyldiphenylamine) and poly(3-methoxydiphenylamine)", J. Electroanal. Chem. Interfac. Electrochem., 289, 37-53 (1990).
P. Chandrasekhar, et al., "Far-IR Transparency and Dynamic Infrared Signature Control with Novel Conducting Polymer Systems," The International Society for Optical Engineering, 2528:169-180 (1995).
Padilla, J; Seshadri, V.; Filloramo, J.; Mino, W.K.; Mishra, S.P.; Radmard, B.; Kumar, A.; Sotzing, G.A.; and Otero, T.F., "High contrast solid-state electrochromic devices from substituted 3,4-propylenedioxythiophenes using the dual conjugated polymer approach," Synthetic Metals 2007, 157, 261-268.
Patil, A.O.; Ikenoue, Y.; Wudl, F.; Heeger A.J., J. Am. Chem. Soc., "Water Soluble Conducting Polymers," 109, 1858 (1987).
Ram, M.K.; Maccioni, E.; Nicolini, C., "The electrochromic response of polyaniline and its copolymeric systems", Thin Solid Films, 303, 27-33 (1997).
Reeves, B.D.; Grenier, C.R.G.; Argun, A.A.; Cirpan, A.; Cunningham, G.B.; McCarley, T.D.; and Reynolds, J.R., "Synthetic Methodology Toward New Propylenedioxythiophene Polymers", Polymer Preprints 45 (1), 284 (2004).
Sapp, S.A.; Sotzing, G.A.; Reynolds, J.R., "High Contrast Ratio and Fast-Switching Dual Polymer Electrochromic Devices", Chem. Mater., 10, 2101-2108 (1998).
Schwendeman, I.; Hickman, R.; Sonmez, G.; Schottland, P.; Zong, K.; Welsh, D.M.; and Reynolds, J.R., "Enhanced Contrast Dual Polymer Electrochromic Devices", Chem. Mater., 14, 3118-3122 (2002).
Tiefenbacher, K.; Rebek, Jr., "Selective Stabilization of Self-Assembled Hydrogen-Bonded Molecular Capsules Through A-A Interactions," J. Am. Chem. Soc. 2012, 134, 2914.
Unur, E.; Jung, J-H.; Mortimer, R.J.; and Reynolds J.R., "Dual-Polymer Electrochromic Film Characterization Using Bipotentiostatic Control", Chem. Mater., 20, 2328-2334 (2008).
Vasilyeva, S.V.; Unur, Ece; Walczak, R.M.; Donoghue E.P.; Rinzler, A.G.; and Reynolds, J.R., "Color Purity in Polymer Electrochromic Window Devices on Indium-Tin Oxide and Single-walled Carbon Nanotube Electrodes", Applied Materials and Interfaces, vol. 1, No. 10, 2288-2297 (2009).
Welsh, D.M.; Kumar, A.; Meijer, E.W.; Reynolds, J.R., "Enhanced Contrast Ratios and Rapid Switching in Electrochromics Based on Poly(3,4-propylenedioxythiophene) Deriatives", Adv. Mat. 11, 1379-1382 (1999).
Youtube Video, "Electrochromic Ballistics Protection Spectacles Prototype," http://www.youtube.com/watch?v=Wn3II82SJXg (Apr. 17, 2013).
Youtube Video, "Electrochromic Glasses Prototype," http://www.youtube.com/watch?v=yDA-Z0YauM0 (Jan. 10, 2013).
Li, H.; Xie, K.; Yao, M.; and Xin, C., "Variable Emissivity Infrared Electrochromic Device Based on Polyaniline Conducting Polymer," Synthetic Metals (2009) 159:1386-1388.
International Search Report dated Feb. 3, 2014 for counterpart PCT Appln. No. PCT/US2013/032320.
Written Opinion of the International Searching Authority dated Feb. 3, 2014 for counterpart PCT Appln. No. PCT/US2013/032320.

(56) References Cited

OTHER PUBLICATIONS

Wermuth. The Practice of Medicinal Chemistry, 1996, chapter 13, pp. 203-237.

Merve Icli-Ozkut et al.; "Substituent and heteroatom effects on the electrochromic properties of similar systems," Journal of Polymer Science Part A: Polymer Chemistry, (2011) 50(4):615-621.

Chad M. Amb et al.; "Propylenedioxythiophene (ProDOT)-phenylene copolymers allow a yellow-to-transmissive electrochrome," Polymer Chemistry, (2011) 2(4): 812.

Extended European Search Report and Written Opinion dated Jun. 9, 2015 for European Patent Application No. 12850225.

K. Krishnamoorthy et al. Rational design of an electrochromic polymer with high contrast in the visible region: dibenzyl substituted poly(3,4- propylenedioxythiophene). Journal Materials Chemistry, vol. 11, issue 12. Oct. 12, 2001.

Javier Padilla, Venkataramanan et al. High contrast solid state electrochromic devices from substituted 3,4-propylenedioxythiophenes using the dual conjugated polymer approach. Synthetic Metals, Issue 157, Apr. 23, 2007.

\* cited by examiner

Schematics Key

Side View
1. Transparent, conductive substrate (e.g. ITO/Mylar)
2. Conducting Polymer (CP) 1
3. CP 2
4. Gaskets
5. Gel or solid electrolyte Top View
1. Typically 10 cm
2. Typically 5 cm

FIGURE 2

Relevant Chemical Structures

*Monomers (l to r):*
2,2'-dibenzyl-3,4-propylene dioxythiophene ("Bz-ProDOT")
2,2'-bis(4-chloro-benzyl-3,4-propylene dioxythiophene ("Cl-Bz-ProDOT")
2,2'-bis(4-amino-benzyl-3,4-propylene dioxythiophene ("NH2-Bz-ProDOT")

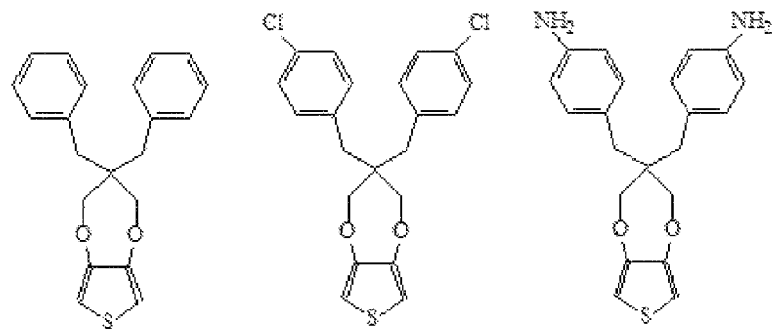

*Monomers (l to r):*
N,N'-diphenyl-benzidine
diphenyl amine
4-amino-biphenyl

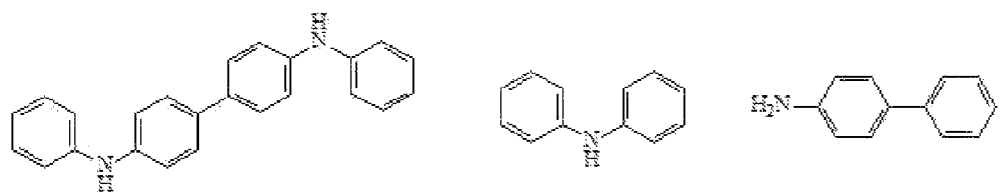

*Diethyl malonate*        *Dibenzyl-substituted diethyl malonate*        *Dibenzyl 1,3-propanediol*

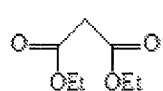 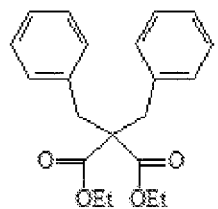 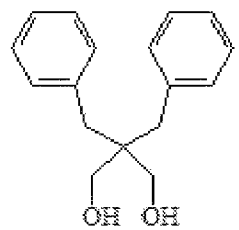

Scheme for Synthesis of Monomer 2,2'-dibenzyl-3,4-propylene dioxythiophene ("Bz-ProDOT"), after Krishnamoorthy et al.

(Target monomer)

FIGURE 4
Scheme for synthesis of 2,2-(bis-4-chlorobenzyl)-3,4-propylenedioxythiophene
("3,3-Bis(4-chlorobenzyl)-3,4-dihydro-2H-thieno[3,4-b][1,4]-dioxepine ",
"Cl-Bz-ProDOT"),
including all intermediates
*Malonate intermediates:*
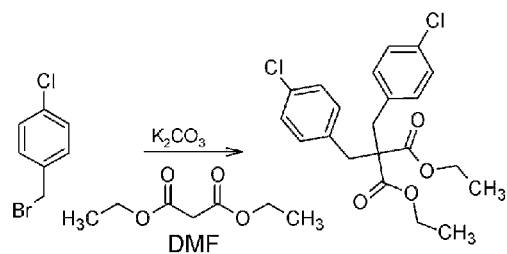
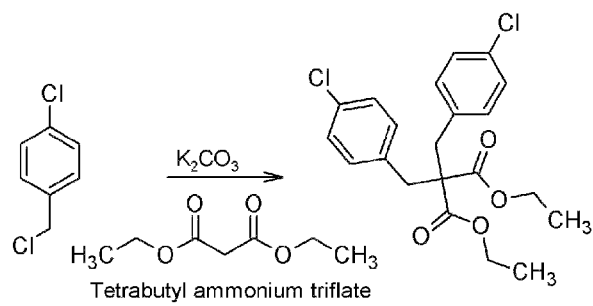

FIGURE 4 (Cont.)
*Propanediol intermediates*
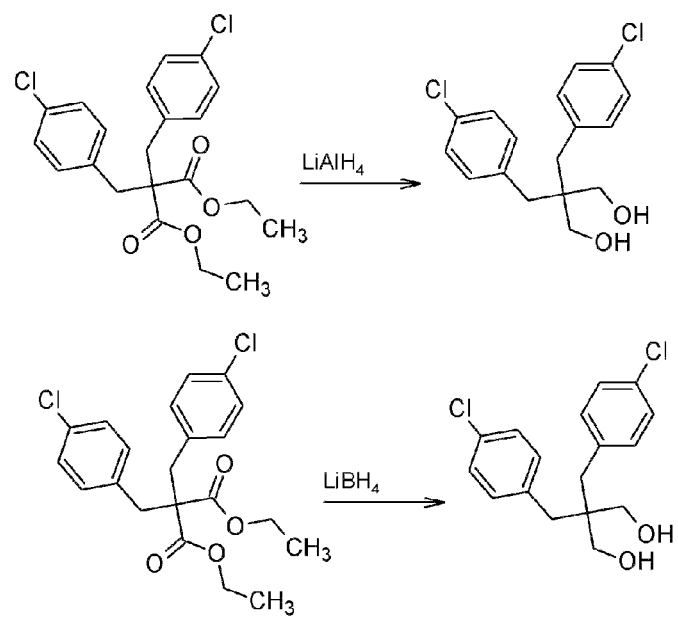
*Final monomer*
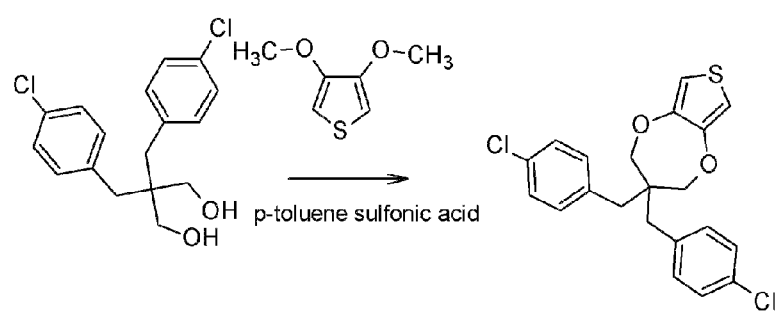

FIGURE 5
Scheme for synthesis of 2,2-(bis-4-bromobenzyl)-3,4-propylenedioxythiophene
("3,3-Bis(4-bromobenzyl)-3,4-dihydro-2H-thieno[3,4-b][1,4]-dioxepine ",
"Br-Bz-ProDOT"),
including all intermediates
*Malonate intermediate:*
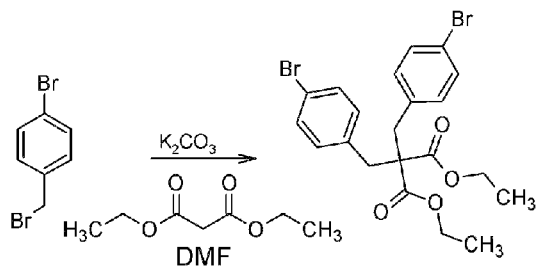
*Propandiol intermediate*
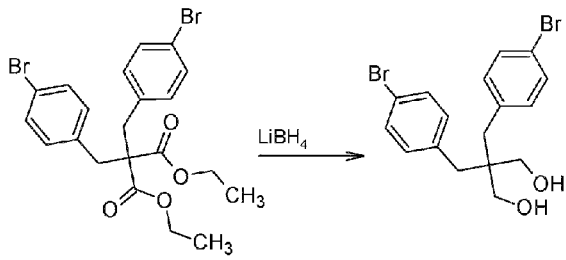

*Final monomer*

FIGURE 6
Scheme for synthesis of 2,2-(bis-4-nitrobenzyl)-3,4-propylenedioxythiophene ("3,3-Bis(4-nitrobenzyl)-3,4-dihydro-2H-thieno[3,4-b][1,4]-dioxepine ", "Nitro-Bz-ProDOT"), including all intermediates
*Malonate intermediates:*
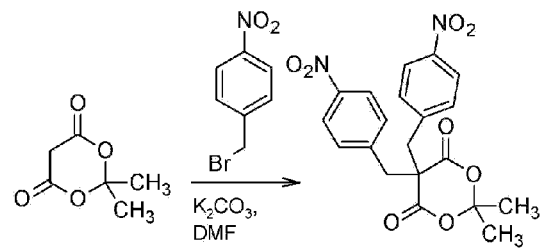
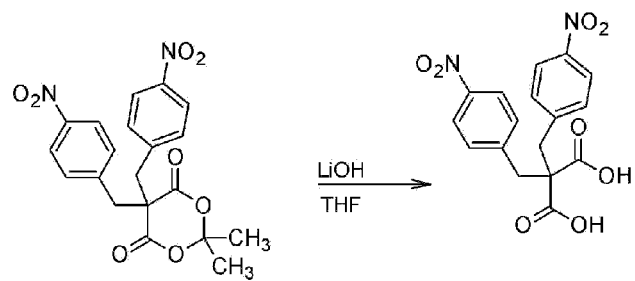

FIGURE 6 (Cont.)
*Propandiol intermediate:*
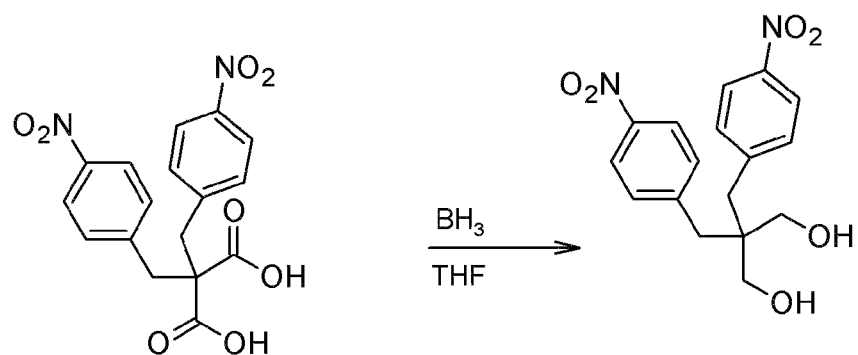
*Final monomer*
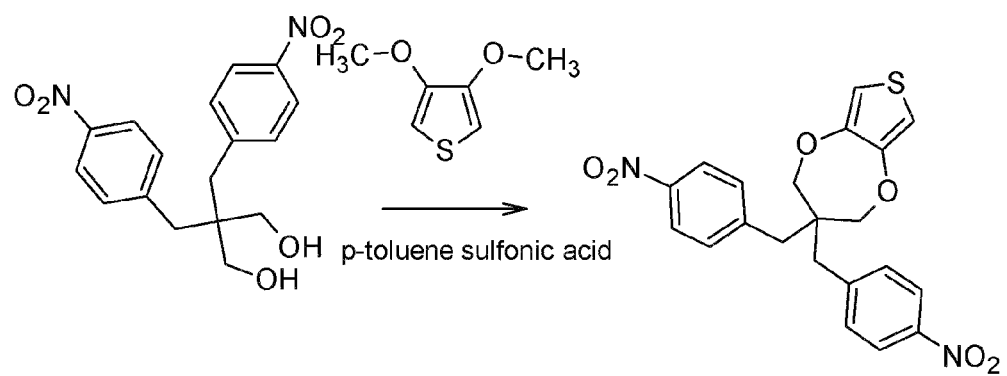

Scheme for synthesis of 2,2-(bis-4-aminobenzyl)-3,4-propylenedioxythiophene
("3,3-Bis(4-aminobenzyl)-3,4-dihydro-2H-thieno[3,4-b][1,4]-dioxepine ",
"Amino-Bz-ProDOT"),
from the corresponding *nitro* monomer

COMPLIMENTARY POLYMER ELECTROCHROMIC DEVICE

REFERENCE TO RELATED APPLICATIONS

This application is a divisional application of U.S. patent application Ser. No. 13/677,197, filed Nov. 14, 2012, which claims the benefit of U.S. Provisional Application No. 61/560,243, filed Nov. 15, 2011, the entirety of which are incorporated by reference herein.

FIELD OF THE INVENTION

Provided are conducting polymer (CP) compositions and electrochromic devices containing the same. More particularly, this invention relates to CP compositions and electrochromic devices responsive in the visible-to-near-IR spectral region.

BACKGROUND OF THE INVENTION

Electrochromic Materials and Devices and Electrochromic Conducting Polymers

Electrochromic materials change color upon application of a voltage, generally a small (<5 V) DC voltage. The "color" change may be in the visible spectral region, but it may also be in the near infrared (NIR), infrared and microwave spectral region. Electrochromic devices may be transmissive-mode, in which light passes through the device and is modulated by the device, and reflective-mode, in which light is reflected off the device and also modulated by the device. Electrochromic devices may be used in windows, rear view automobile mirrors, flat panel displays, variable emittance materials for spacecraft application, and infrared camouflage.

The change in color of an electrochromic material is usually due to a reduction/oxidation ("redox") process within the electrochromic material. Electrochromic materials active in the visible spectral region include metal oxides, such as tungsten, molybdenum, nickel and tantalum oxides, showing a transition from highly colored to near transparent depending on the potential (voltage) applied to them.

Another class of electrochromic materials are conducting polymers. Redox of a conducting polymer, which changes its color as well as conductivity, is usually accompanied by an inflow or outflow of counterions in the conducting polymer known as "dopants". Common dopant counterions include $ClO_4^-$ and $BF_4^-$. As examples, the conducting polymer poly(pyrrole) is dark blue and conductive in its oxidized ("doped" or "colored") state and pale-green in its reduced ("de-doped" or "undoped") state, and the conducting polymer poly(aniline) is nearly transparent in its reduced state, transitioning to green or dark green in its oxidized state. An electrochromic material is said to be "anodically coloring" if application of a positive voltage to it causes it to transition to a colored or dark state, and "cathodically coloring" if application of a negative voltage causes it to transition to a colored or dark state. Poly(pyrrole) and poly(aniline) are anodically coloring polymers.

The most convenient and common method of synthesis of conducting polymers for electrochromic uses is electropolymerization from a solution of the monomer directly onto a conductive, transparent substrate, such as indium-tin-oxide (ITO) on glass, poly(ethylene terephthalate) (PET, "Mylar") or other transparent plastic substrate. The electro-polymerization may be carried out using a constant applied potential (potentiostatic mode), a potential sweep (potential sweep mode) or other applied potential programs. Thus, e.g., poly(diphenyl amine) may be electrochemically deposited onto ITO/glass or ITO/PET from a 0.05 M solution of the monomer in acetonitrile at about +0.8 V (potentiostatic mode).

A common transmissive-mode electrochromic device is fabricated by depositing an electrochromic material on a conductive, transparent substrate, such as ITO/glass or ITO/PET, forming the active or working electrode. A similar substrate, ITO/glass, comprises the opposing or counter electrode. A liquid, solid or gel electrolyte is disposed as a layer between the two electrodes or incorporated into the polymers. The active electrochromic material on the working electrode may be switched to a dark "colored" or a less colored "bleached" state, depending on the voltage applied to it in this 2-electrode device, thus modulating the transmission through the device. A common reflective-mode electrochromic device may be fabricated in a similar fashion, with the difference that, in place of the transparent, conductive substrate, an opaque, conductive substrate, such as Au deposited on a microporous membrane, may be used. The counter electrode in such a device may be a similar conductive substrate disposed behind the working electrode. Such a reflective mode device is described in U.S. Pat. No. 5,995,273 (1999) and U.S. Pat. No. 6,033,592 (2000), issued to Chandrasekhar (collectively, the "Chandrasekhar IR patents").

In the operation of such devices as described in the preceding paragraph, a voltage is applied to the working electrode. As an example, if the active electrochromic material thereon is anodically coloring, then a positive voltage will cause it to transition to a colored state. In the case of a conducting polymer, a corresponding inflow of counterions, in this case anions, will occur into the polymer.

In all 2-electrode electrochromic devices, at the same time that the working electrode experiences a (+) voltage, the counter electrode experiences the identical (−) voltage, and vice versa. An electrochemical reaction will then need to occur at the counter electrode to balance the charge transfer corresponding to the reaction occurring at the working electrode; the availability of a suitable counter electrode reaction is vital to the reversible functioning of the electrochromic device. In the case where the counter electrode substrate is bare or naked, i.e. it does not have an electrochemically active material such as an electrochromic material deposited on it, the likely electrochemical reaction that occurs is reduction of impurities present in the electrolyte, including, by way of example, dissolved gases (including oxygen); in the case of dissolved oxygen, species such as the superoxide ion or radical oxygen species may then be generated which have lifetimes as long as 20 seconds and which oxidatively or reductively degrade the active electrochromic material present on the other electrode (Menon et al., 1998) (Chandrasekhar IR patents, Chandrasekhar et al. 2002, Chandrasekhar et al. 1987). In such a circumstance, the overall electrochemical processes occurring within the electrochromic device are said to exhibit poor reversibility. This leads to a number of detrimental results, e.g. much more rapid degradation of the active electrochromic material and much slower electrochromic switching time.

Anodically-Coloring Conducting Polymers

Anodically-coloring conducting polymers described include poly(aniline), poly(pyrrole) as well as the structurally related series comprising poly(diphenyl amine), poly (4-amino-biphenyl) (Dao and coworkers (Guay et al., 1988, 1989, LeClerc et al., 1988, Nguyen et al., 1990)) and poly(N,N'-diphenyl benzidine) (Suzuki et al., U.S. Pat. No.

4,874,481 (1989)). These polymers show a color transition from nearly transparent in their reduced state to dark blue or blue-green in their oxidized state, with modest but consistent light/dark contrast, Delta % -Transmission between light/dark states at 575 nm being ca. 40%. Furthermore, the voltages required for their switching are relatively low, less than +1.5 V in many cases (in a 2-electrode-mode device with a bare ITO/substrate electrode serving as the counter electrode). An additional, key advantage of this series of poly(aromatic amine) polymers is that they are nearly transparent or, in some cases, completely transparent in their fully reduced state.

These polymers do however show a number of drawbacks, the most important of which is that, when incorporated into an electrochromic device without the presence of a suitable, complimentary counter electrode reaction, they display very slow light/dark switching times (up to 25 seconds) and modest contrast; they also then start to degrade after about 1000 cycles of light/dark switching. (Reasons for degradation include the lack of a counter-electrode reaction, resulting in impurities or water/oxygen in the electrolyte undergoing redox at the counter electrode; these may in turn generate harmful species, e.g. $O_2^-$, which further degrade the polymer). Nevertheless, these poly(aromatic amines) constitute an ideal set of anodically coloring electrochromic polymers, if they could be paired with a well-performing set of cathodically coloring electrochromic polymers in a single electrochromic device.

Cathodically Coloring Electrochromic Conducting Polymers and Structure-Performance Relationships Therein In terms of cathodically coloring electrochromic conducting polymers, a number of these are described in the patent and journal literature. One of the first such polymers was poly(isothianaphthene) (first synthesized by Wudl and coworkers (Hotta et al., 1987, Patil et al., 1987) and with subsequent improvements in processing by Chandrasekhar et al., 1990), which transitions from a translucent blue-green in its oxidized state to a deep blue in its reduced state. Among its drawbacks was a relatively poor light/dark contrast (Delta % T typically 20% at wavelength of maximum absorption), asymmetric switching voltages (+1.3 V fully oxidized, −0.5 V fully reduced, all vs. Ag/AgCl), and rapid degradation (<200 cycles), i.e. poor "cyclability".

A series of cathodically coloring polymers based on poly(3,4-ethylenedioxythiophene) (PEDOT) and on other polymers containing the thiophene moiety have been described by Groenendal et al., (2000), Sapp et al. (1998), Gazotti et al. (1998) and others. These yield a variety of colors in their colored state, including yellow, red, blue and blue-black. Among their drawbacks are modest light/dark contrast, large and asymmetric switching voltages, and modest cyclability. These polymers are generally not transparent in their light state, but rather lightly colored, semi-translucent, the colors varying from undesirable reds, yellows and blues to desirable grays.

With respect to the search for better cathodically coloring polymers, then, the propylene analogues of PEDOT, derivatives of poly(3,4-propylenedioxythiophene) (PProDOT), show improved electrochromic performance over PEDOT derivatives. Welsh et al. (1999) describe a dimethyl-substituted derivative of PProDOT with high light/dark contrast, with claimed Delta-% T ca. 65% at ca. 610 nm (the wavelength of highest absorption of the polymer); their Delta-% T numbers are however of electrochromic devices incorporating the polymer which are subtracted for the absorption of the substrates, i.e. they give the absorption due to the polymer alone, with the substrates rather than air used as reference; based on the expected absorptions for the substrates they use, the Delta-% T for the dimethyl-substituted PProDOT is closer to 38% for the actual device against air (rather than substrate) reference. Nevertheless, Welsh et al. demonstrate, in a comparison of the electrochromic properties of the dimethyl-PProDOT with the unsubstituted PProDOT that the substitution, in this case 2,2' dimethyl substitution, on the propylene of the ProDOT monomer yields significant improvement of the electrochromic properties of the resulting polymer, such as improved light/dark contrast and a lower and more symmetric switching voltage (in the case of dimethyl-PProDOT, a convenient ca. +/−1.0 V).

Krishnamoorthy et al. disclose dibenzyl-substituted derivatives of PProDOT, which are also cathodically coloring conducting polymers; these appear to the best reported electrochromic performance to date for cathodically coloring conducting polymers, although again, the data are quoted vs. substrate rather than air reference so actual performance must only be estimated. The wavelength of highest absorbance of this polymer in its dark state is ca. 630 nm. Switching times of <5 seconds are reported. An advantageous feature of this polymer is that, like its dimethyl-substituted analog (Welsh et al., 1999, discussed above), it switches at low, symmetrical voltages, about +/−1.0 V. This dibenzyl PProDOT ("P(DiBz-ProDOT)") thus appears to be very well suited for use as the cathodically coloring counterpart in a complimentary-polymer electrochromic device also incorporating a well-performing anodically coloring polymer. Its wavelength of highest absorbance (630 nm) is a little on the higher wavelength side, close to the near-IR; if this could be shifted to near 550 nm, more towards the green, perhaps by a fortuitous substitution on the benzyl ring, it would constitute an ideal cathodically-coloring polymer.

Complimentary Electrode (e.g. Dual Polymer) Electrochromic Devices

Electrochromic devices incorporating complimentarily-coloring (i.e., anodically and cathodically coloring) electrochromic materials may show improved performance over devices containing a single (either anodically or cathodically coloring) electrochromic material. Set forth here now are examples of such improved performance in actually reported data to date.

For example, a complimentary electrochromic device based on poly(o-methoxyaniline) doped with p-toluene sulfonic acid (PoANis-TSA) as the anodically coloring polymer and a blend of poly(4,4'-dipentoxy-2,2'-bithiophene) (PET2) and poly(epichlorohydrin-co-ethylene oxide) (Hydrin-C) is described in a publication of Gazotti et al. (1998). In this device, moderate light/dark contrast, Delta % T=32% at 620 nm (though again vs. a substrate reference rather than an air reference) is coupled with very fast switching time, <2 seconds, as is to be expected for such a complimentary polymer device based on the discussion above. As another example, complimentary polymer devices based on co-polymers of ethylene-dioxythiophene derivatives with N-methylcarbazole are described in a publication of Sapp et al. In this work, twelve complimentary polymer pairs are studied, all having EDOT derivatives as the cathodically coloring component. The best switching time reported in this work is ca. 3 seconds and the best light/dark contrast, Delta-% T, of 63% at 650 nm, the wavelength of highest absorbance (although this is again with device substrate rather than air as reference): A correction for the substrate absorption yields a corrected Delta-% T of 40% (vs. 63% uncorrected). Additionally, the very high wavelength of highest absorption (650 nm, in the red and close to the near-IR boundary) and the narrow rather than broad-band nature of the absorption is a serious drawback of the best of these 12 complimentary-polymer devices. In another example, Groenendal et al. claim light/dark contrasts as high as 45% at 620 nm for one P(EDOT) polymer in a complimentary polymer device; again, however, these values represent substrate-subtracted spectra, and actual contrasts (i.e. against air reference) are closer to 30% for this polymer.

In yet another example of complimentary-electrochromic devices U.S. Pat. No. 6,859,297 (2005), issued to Lee et al., discloses an amorphous, anodically coloring electrochromic material comprising nickel oxide doped with tantalum. This material is deposited on a transparent, conductive substrate. Notably, it is coupled with a cathodically coloring material, such as electrochromic material based on tungsten oxide, yielding a complimentary-electrochromic device having cathodically and anodically electrochromic materials in the same device. The composite device is shown to be significantly superior in performance to single-electrochromic (either cathodically or anodically coloring) devices.

The complimentary-polymer electrochromic devices and systems discussed above however, have very significant drawbacks. The first of these drawbacks is that the complimentary polymers are not well matched in terms of the potential at which they undergo oxidation/reduction. As an example, in its cyclic voltammogram, the cathodically-coloring poly(isothianapthene) shows two sharp oxidation peaks between +0.5 and +1.2 V, a reduction peak at ca. +0.8 V, and another reduction peak at ca. +0.4 V, all vs. Ag/AgCl (Chandrasekhar, 1990). In comparison, the anodically-coloring poly(diphenyl amine) and poly(4-amino-biphenyl) both show oxidation peaks at ca. +0.5 V and ca. +0.8 V and reduction peaks at ca. +0.8 V and +0.5 V (all vs. Ag/AgCl) (Guay et al. 1989). Similarly, the anodically-coloring poly (N,N'-diphenyl benzidine) shows a single oxidation peak at ca. +1.4 V and a single reduction peak at ca. 0.0 V (all vs. Ag/AgCl) (Chandrasekhar et al., 1991). Thus, even with a small shift expected in dual-polymer devices, these anodically-coloring polymers would make a very poor match for the cathodically-coloring poly(isothianaphthene). When the anodically coloring polymer of the pair is fully oxidized at the most extreme (+) voltage usable for the pair, the cathodically coloring polymer may only be partially reduced and so not able to contribute fully to the electrochromic contrast. Indeed, such a "mismatch" situation for most prior-art cathodically-coloring and anodically-coloring polymers may be demonstrated by experiment.

A second drawback of these complimentary-polymer systems is that nearly all of the cathodically-coloring polymers used do not themselves (i.e. on their own, in single-polymer devices) show significant light/dark contrast; they also frequently show narrow-band absorption. On the rare occasions that a high-contrast cathodically coloring polymer, such as the dibenzyl-PProDOT (P(DiBz-ProDOT)) referenced above, has been used in a complimentary polymer device, it has been paired with poorly matched anodic conducting polymers which also display mediocre electrochromic performance. See, e.g., Invernale et al. (2009) and Padilla et al. (2007). Additionally, nearly all cathodically-coloring polymers used in such devices are not transparent in their light state, but rather translucent, with significant, sometimes undesirable (e.g. light green or blue) coloration. Yet further, except in rare cases such as the P(DiBz-ProDOT) cited above, cathodically-coloring polymers used in complimentary devices to date generally have narrow band absorption which is frequently in the red region, with the wavelength of highest absorption generally in the 620 to 650 nm range.

A third drawback of these prior art complimentary-polymer systems, related to the first two, is that the redox reactions of the pair are not matched in terms of number of electrons involved. For example in the cited study of Sapp et al. (1998), the anodically coloring redox reaction in many of the pairs studied is a 2-electron reaction whilst the cathodically coloring reaction is a 1-electron reaction. Such a mismatch generates significant overpotential which reduces the electrochromic efficiency of the device.

Accordingly, there is a significant need in the art for dual-polymer devices that are capable of overcoming the aforementioned deficiencies.

SUMMARY OF THE INVENTION

In general terms, the present invention provides dual-polymer electrochromic devices which overcome the drawbacks of prior-art dual-polymer devices, as described at length in the discussion above. Moreover, the present invention provides novel cathodically-coloring polymers especially suitable for such dual-polymer devices. Indeed, the present invention provides cathodically-coloring polymers that are well matched electrochromically and electrochemically to appropriate anodically-coloring polymers, as described in more detail below.

In a first embodiment, the present invention provides a complimentary electrochromic device comprising:

(a) a first electrode comprising a cathodically coloring conducting polymeric material, the cathodically coloring conducting polymeric material comprising a substituted or unsubstituted 2,2-dibenzyl-3,4-propylenedioxythiophene monomer;

(b) a second electrode comprising an anodically coloring conducting polymeric material;

(c) an electrolyte disposed between and in electrochemical communication with the first electrode and the second electrode; and wherein the redox potential of the cathodically coloring conducting polymeric material is substantially matched to the redox potential of the anodically coloring conducting polymeric material such that when one said polymeric material is fully oxidized, the other said polymeric material is fully reduced.

In one aspect of the device, at least one benzyl moiety of the substituted 2,2-dibenzyl-3,4-propylenedioxythiophene is para substituted with a substituent selected from the group consisting of halo, sulfonyl, nitro, and alkyl. In preferred aspects, the benzyl moiety of the substituted 2,2-dibenzyl-3,4-propylenedioxythiophene is substituted with a chloro or bromo substituent.

In another aspect of the device, the cathodically coloring conducting polymeric material may comprise a copolymer. In a further aspect, the polymeric material may comprise poly(2,2-dibenzyl-3,4-propylenedioxythiophene), poly(2,2-bis(4-chloro-benzyl)-3,4-propylenedioxythiophene), poly(2,2-bis(4-bromo-benzyl)-3,4-propylenedioxythiophene), poly(2,2-bis(4-nitro-benzyl)-3,4-propylenedioxythiophene), or combinations thereof. In yet another aspect, the cathodically coloring conducting polymeric material may comprise at least one monomer selected from the group consisting of 2,2-bis(4-chloro-benzyl)-3,4-propylenedioxythiophene, 2,2-bis(4-bromo-benzyl)-3,4-propylenedioxythiophene, and combinations thereof. In another aspect the cathodically conducting polymeric material may comprise a copolymer of the monomers 2,2-dibenzyl-3,4-propylenedioxythiophene, 2,2-bis(4-chloro-benzyl)-3,4-propylenedioxythiophene), and 2,2-bis(4-bromo-benzyl)-3,4-propylenedioxythiophene). Additionally, the cathodically conducting polymeric material may comprise a copolymer of the monomers 2,2-dibenzyl-3,4-propylenedioxythiophene, 2,2-bis(4-chloro-benzyl)-3,4-propylenedioxythiophene), and 2,2-bis(4-bromo-benzyl)-3,4-propylenedioxythiophene), in a molar ratio in the range of 1:1:1 to 50:7:1, respectively.

In a still further aspect of the device, the anodically coloring conducting polymeric material may comprise a poly(aromatic amine). In other aspects, the anodically conducting polymeric material comprises a copolymer. In preferred aspects, the anodically conducting polymer material may comprise at least one monomer selected from the group consisting of N,N'-diphenyl benzidine, diphenyl amine, 4-aminobiphenyl, and combinations thereof. In a more preferred aspect, the anodically coloring conducting polymeric material comprises a copolymer of the monomers N,N'-diphenyl benzidine, diphenyl amine and 4-aminobiphenyl in a molar ratio in the range of 1:1:1 to 50:1:1, respectively.

In other aspects of the device, the first and/or second electrode comprises a first and/or second conductive transparent substrate. In another aspect, the first and/or second conductive substrate may comprise indium-tin-oxide(ITO)/glass, ITO/poly(ethylene terephthalate)(PET), tin-oxide/glass, tin-oxide/PET, gold/glass, carbon-nanotubes/glass, carbon-nanotubes/PET, gold/PET, or a combination thereof. Additionally, in some aspects of the device, the electrolyte may comprise a liquid electrolyte, solid electrolyte, gel electrolyte, or a combination thereof.

In another embodiment, the instant invention encompasses a method for obtaining a complimentary electrochromic device comprising the steps of:

(a) preparing a first electrode by depositing a cathodically coloring conducting polymeric material on a first transparent conductive substrate to obtain the first electrode, wherein the cathodically coloring conducting polymeric material comprises a substituted or unsubstituted 2,2-dibenzyl-3,4-propylenedioxythiophene monomer;

(b) preparing a second electrode by depositing an anodically coloring conductive polymeric material on a second transparent conductive substrate to obtain the second electrode, wherein the anodically coloring conductive polymer material comprises a poly(aromatic amine);

(c) superimposing the first electrode and the second electrode and providing a space between the first and second electrodes; and (d) placing an electrolyte in the space between the first and second electrodes to provide the electrochromic device, wherein the electrolyte is in electrochemical communication with the first and second electrodes.

In further embodiments, the invention provides a compound of the formula:

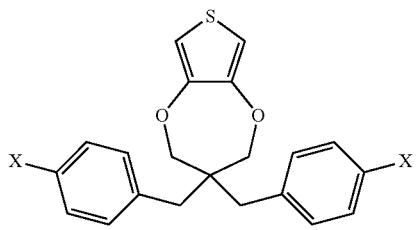

wherein X is an electron-withdrawing substituent. In certain aspects, X is a substituent selected from the group consisting of cyano, sulfoxy, carboxy, carboxylate, aldehyde, carbonyl, halo, alkyl, sulfonyl, nitro, and amino.

In another embodiment, the present invention provides a method for preparing 2,2-bis(4-X-benzyl)-3,4-propylenedioxythiophene, wherein X is a substituent selected from the group consisting of halo, alkyl, sulfonyl, nitro, and amino, comprising the steps of reacting the 2,2-bis(4-X-benzyl)-3,4-propanediol with 3,4-dimethoxythiophene under conditions effective to yield 2,2-bis(4-X-benzyl)-3,4-propylenedioxythiophene. In other embodiments, the instant invention provides a substituted dibenzyl 1,3-propanediol wherein the para position of at least one benzyl moiety is substituted with a substituent selected from the group consisting of halo, sulfonyl, nitro, amino, and alkyl, and a method of preparing the same.

In still another embodiment, the present invention provides a method for preparing an electrode, comprising the steps of:

(a) providing a deposition solution comprising at least one monomer of a cathodically coloring polymeric material, wherein the at least one monomer comprises 2,2-bis(4-X-benzyl)-3,4-propylenedioxythiophene, wherein X is a substituent selected from the group consisting of halo, alkyl, sulfonyl, and nitro; and (b) uniformly depositing the cathodically coloring conducting polymer material onto a transparent conductive substrate to provide the electrode.

In an additional embodiment, the present invention provides a method for preparing an electrode, wherein the electrode comprises a polymer of N,N'-diphenyl benzidine monomer, the method comprising the steps of:

(a) providing a deposition solution comprising the N,N'-diphenyl benzidine monomer;

(b) uniformly depositing the polymeric material onto a substrate in contact with the deposition solution to yield the electrode; and wherein the deposition solution comprises dimethylformamide and acetonitrile in a ratio of at least about 6:1 by volume, respectively.

DESCRIPTION OF THE DRAWINGS AND FIGURES

The following description will be more easily understood when read in conjunction with the accompanying figures in which:

FIG. 2 is a representation of the chemical structures of the various monomers and other relevant moieties as described in the present invention.

FIG. 4 shows the synthetic scheme for synthesis of the monomer 2,2-(bis-4-chlorobenzyl)-3,4-propylenedioxythiophene (also called "3,3-Bis(4-chlorobenzyl)-3,4-dihydro-2H-thieno[3,4-b][1,4]-dioxepine" or "Cl-Bz-ProDOT"), according to the present invention.

FIG. 6 shows the synthetic scheme for synthesis of the monomer 2,2-(bis-4-nitrobenzyl)-3,4-propylenedioxythiophene (also called "3,3-Bis(4-nitrobenzyl)-3,4-dihydro-2H- thieno[3,4-b][1,4]-dioxepine" or "Nitro-Bz-ProDOT, according to the present invention.

Figure 7:
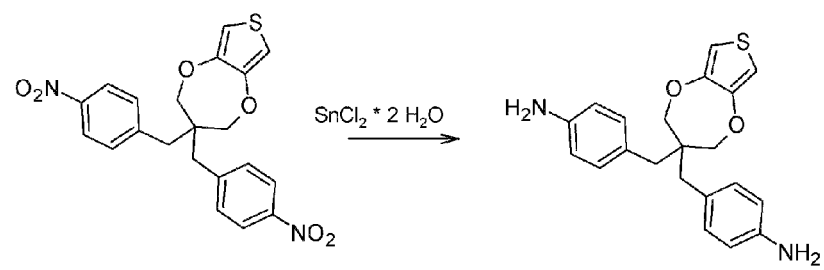
Figure 8:
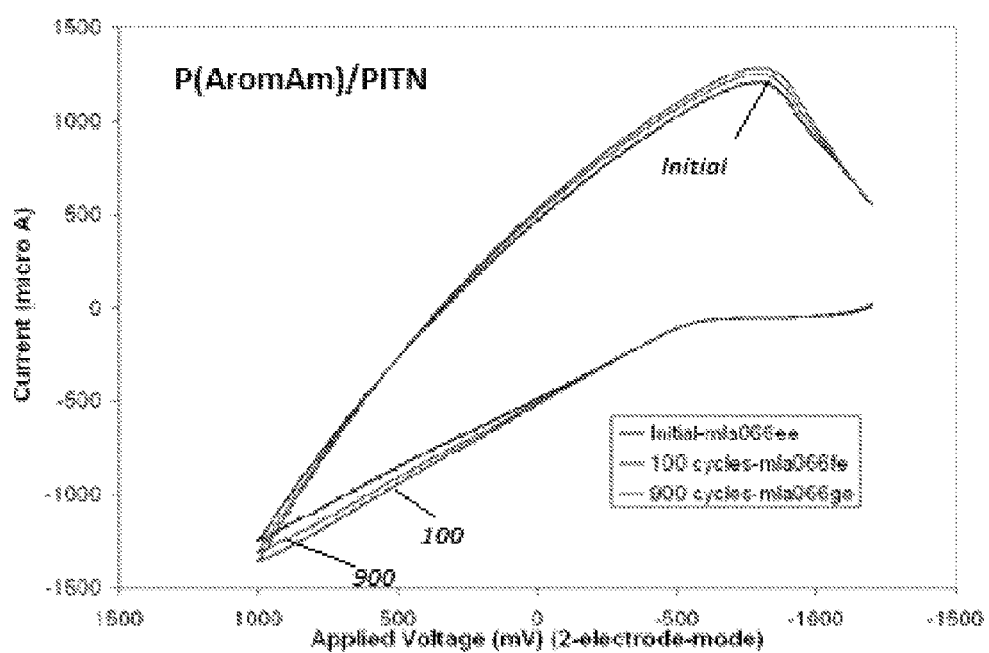

FIG. 7 shows the synthetic scheme for synthesis of the monomer 2,2-(bis-4-aminobenzyl)-3,4-propylenedioxythiophene ("3,3-Bis(4-aminobenzyl)-3,4-dihydro-2H-thieno[3,4-b][1,4]-dioxepine" or "Amino-Bz-ProDOT"), according to the present invention FIG. 8 shows cyclic voltammograms of the electrochromic device as assembled in COMPARATIVE EXAMPLE 16, wherein poly(isothianaphthene) (PITN) is the cathodically-coloring polymer and a copolymer of N,N'-diphenyl benzidine, diphenyl amine and 4-amino-biphenyl is the anodically-coloring polymer, between the voltages corresponding to its extreme light and dark states.

Figure 9:
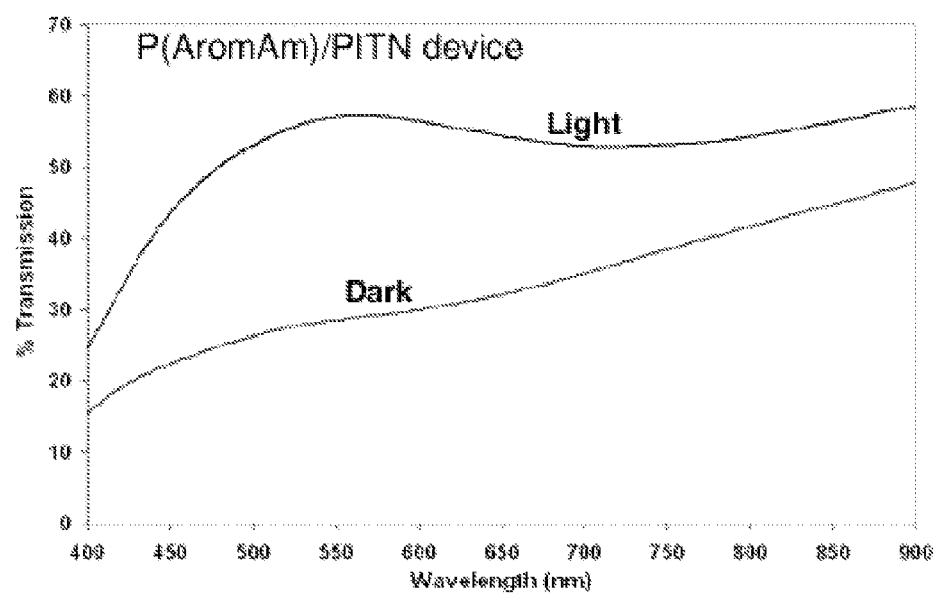

FIG. 9 shows the UV-Vis-NIR spectra of the electrochromic device as assembled in COMPARATIVE EXAMPLE 16, wherein PITN is the cathodically-coloring polymer and a copolymer of N,N'-diphenyl benzidine, diphenyl amine and 4-amino-biphenyl is the anodically-coloring polymer, in its extreme light and dark states.

Figure 10:
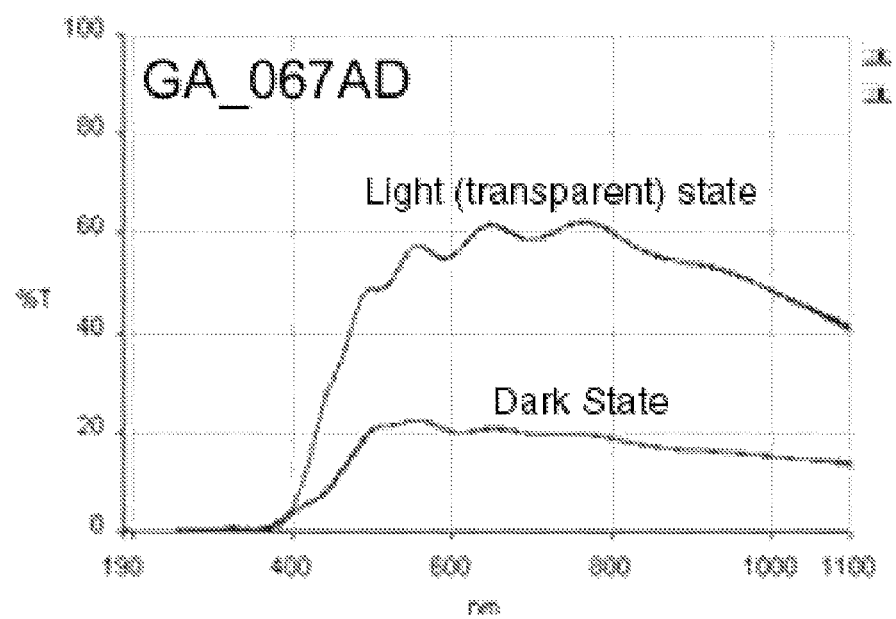

FIG. 10 shows the UV-Vis-NIR spectra of the electrochromic device assembles as in COMPARATIVE EXAMPLE 17, demonstrates a single-polymer electrochromic device comprising poly(N,N'-diphenyl benzidine), in its extreme light and dark states.

Figure 11:
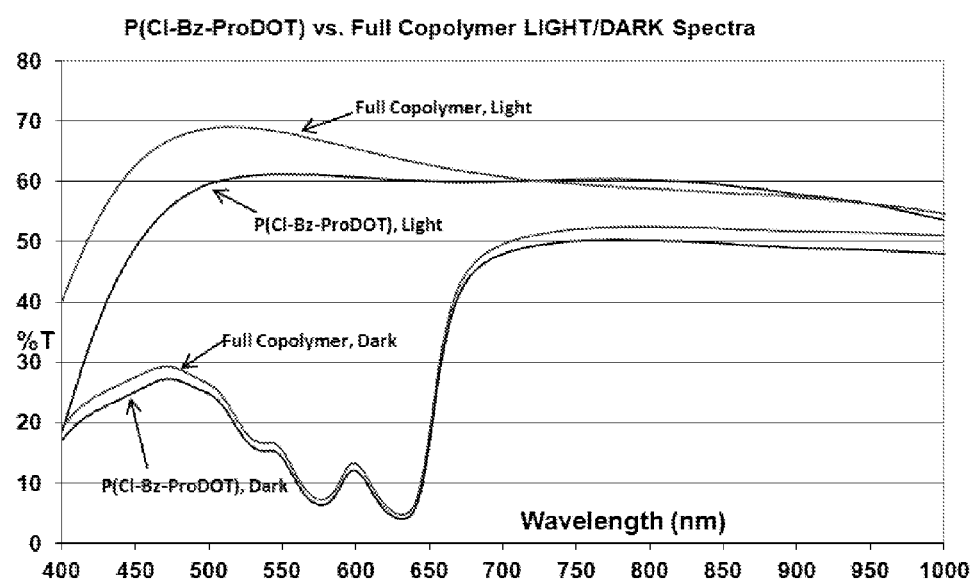

FIG. 11 comparatively shows the UV-Vis-NIR spectra in the extreme light/dark states of two electrochromic devices: (1) A device assembled according to COMPARATIVE EXAMPLE 15, wherein poly(2,2-(bis-4-chloro-benzyl)-3,4-propylenedioxythiophene) ("Poly(Cl-Bz-ProDOT)") is the cathodically coloring polymer and a copolymer of N,N'-diphenyl benzidine, diphenyl amine and 4-amino-biphenyl is the anodically coloring polymer. (2) A device assembled according to EXAMPLE 14, wherein a copolymer of 2,2-(bis-4-chloro-benzyl)-3,4-propylenedioxythiophene, 2,2-(bis-4-bromo-benzyl)-3,4-propylenedioxythiophene and 2,2dibenzyl-3,4-propylenedioxythiophen is the cathodically-coloring polymer and a copolymer of N,N'-diphenyl benzidine, diphenyl amine and 4-amino-biphenyl is the anodically-coloring polymer.

Figure 12:
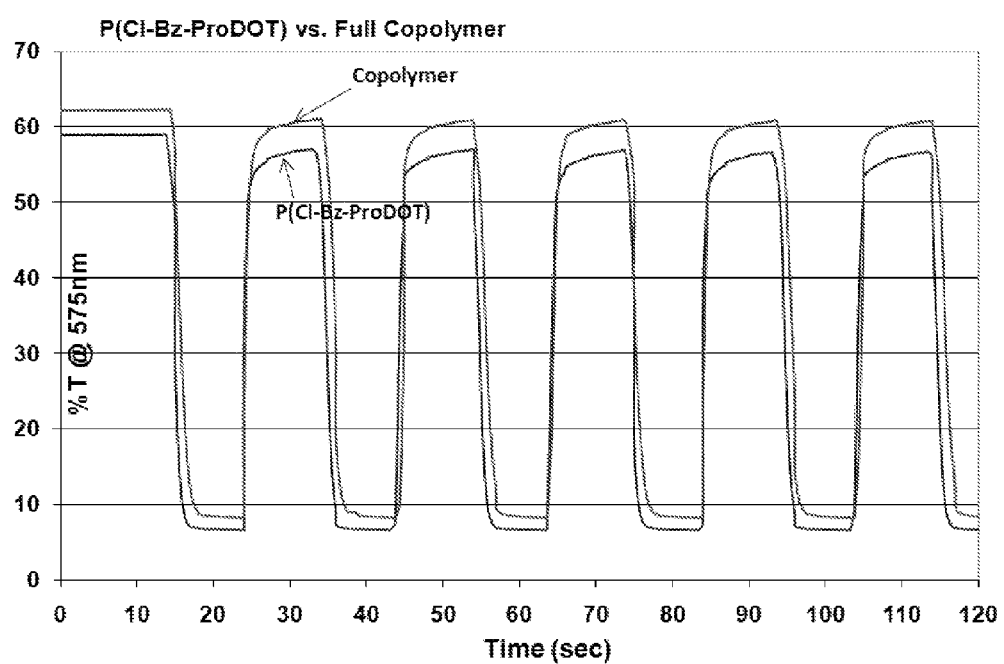

FIG. 12 shows the corresponding switching time data for the same devices as seen in FIG. 11.

Figure 13:
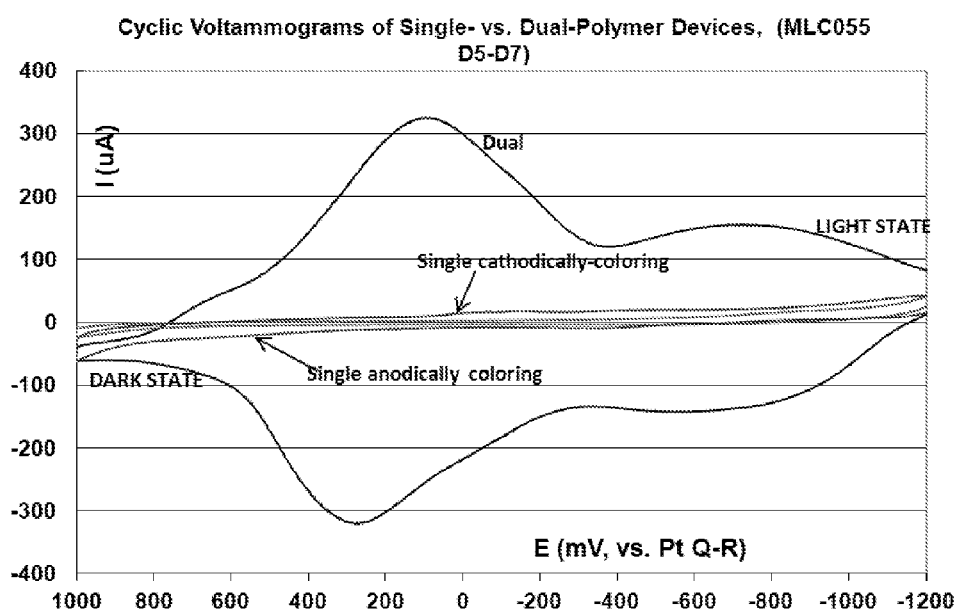

FIG. 13 comparatively shows cyclic voltammetric data for: (1) A single-polymer, cathodically-coloring electrode having a copolymer of 2,2-(bis-4-chloro-benzyl)-3,4-propylenedioxythiophene, 2,2-(bis-4-bromo-benzyl)-3,4-propylenedioxythiophene and 2,2-dibenzyl-3,4-propylenedioxythiophene as the polymer. (2) A single-polymer, anodically-coloring device having a copolymer of N,N'-diphenyl benzidine, diphenyl amine and 4-amino-biphenyl as the polymer. (3) A composite, dual-polymer device incorporating these two individual polymers.

Figure 14:
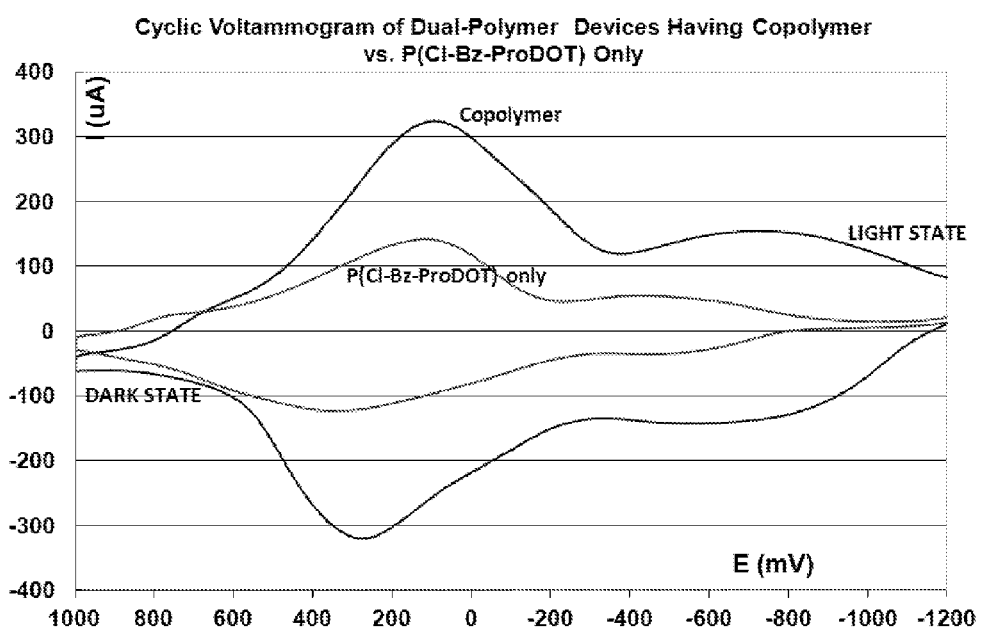

FIG. 14 shows cyclic voltammetric data for: (1) A dual polymer device in which the cathodically-coloring polymer is poly(2,2-(bis-4-chloro-benzyl)-3,4-propylenedioxythiophene) and the anodically coloring polymer is a copolymer of N,N'-diphenyl benzidine, diphenyl amine and 4-amino-biphenyl. (2) A dual polymer device in which the cathodically-coloring polymer is a copolymer of 2,2-(bis-4-chloro-benzyl)-3,4-propylenedioxythiophene, 2,2-(bis-4-bromo-benzyl)-3,4-propylenedioxythiophene and 2,2-dibenzyl-3,4-propylenedioxythiophene. The total charge deposited during the polymerizations of the cathodically-coloring polymers in both devices were nearly identical, as were those for the anodically-coloring polymers in both devices.

Figure 15:
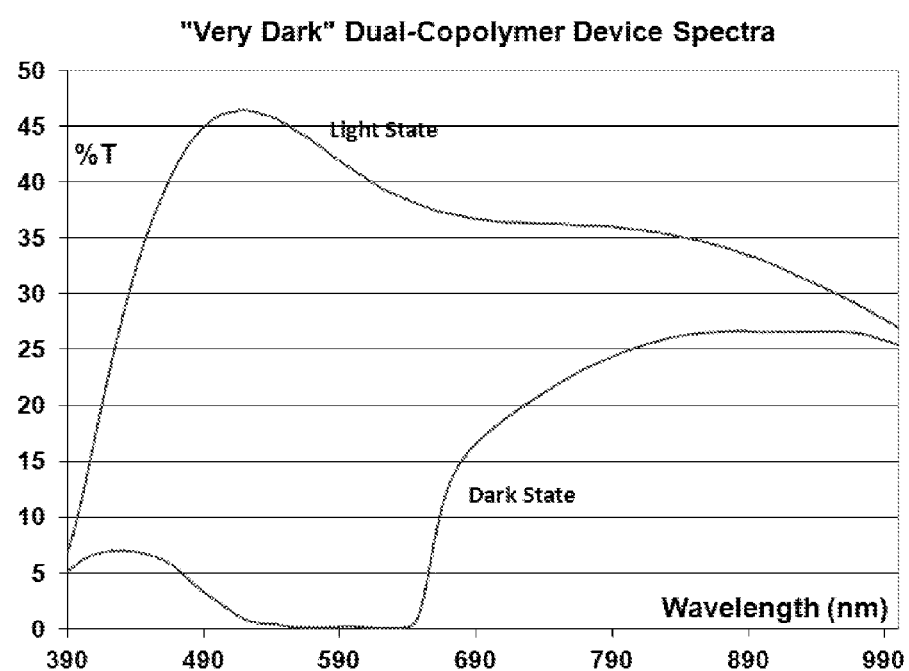

FIG. 15 shows the UV-Vis-NIR spectra in the extreme light/dark states of the device assembled according to EXAMPLE 14, wherein a copolymer of 2,2-(bis-4-chloro-benzyl)-3,4-propylenedioxythiophene, 2,2-(bis-4-bromo-benzyl)-3,4-propylenedioxythiophene and 2,2-dibenzyl-3,4-propylenedioxythiophene is the cathodically-coloring polymer and a copolymer of N,N'-diphenyl benzidine, diphenyl amine and 4-bromo-biphenyl is the anodically-coloring polymer, but with the difference that the total charge deposited for both the cathodically- and anodically-coloring polymers was ca. 17% greater.

DETAILED DESCRIPTION OF THE INVENTION

While the compositions, methods and devices heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Unless defined otherwise, all technical and scientific terms used herein have the same meaning as commonly understood by one of ordinary skill in the relevant art. Although any methods and materials similar or equivalent to those described herein can also be used, the preferred methods and materials are now described.

Where an electrochemically active material possessing highly reversible electrochemical activity is introduced on a counter electrode it may be configured to act in a complimentary and highly reversible fashion to the material at a working electrode. For example, when the electrochromic material at the working electrode undergoes oxidation, the complimentary material at the counter electrode would undergo reduction, and vice versa. This leads to a highly reversible electrochemical system where the active electrochromic displays much more rapid switching times, higher light/dark contrast, highly reversible switching and little degradation over a very large number of switching cycles. This is the principle behind complimentarily coloring electrochromic devices.

The simplest and most efficient of such complimentarily coloring device is one in which the same electrochromic material is disposed on both the working and counter electrode. Such a system, where the electrochromic on one electrode undergoes a redox process "equal and opposite" to that at the other electrode, is by definition highly reversible. Such a system would work well for a reflective-mode electrochromic device. However, it would be useless for a transmissive-mode (see-through) device, since the overall device would not change color at all: One electrode's darkness would compensate for the other electrode's lightness. However, if one of the electrochromic materials shows activity that is opposite to that of the other, e.g. it turns to its light state on application of a (+) voltage while the other material turns dark on application of a (+) voltage, then this would yield a functioning transmissive-mode, complimentarily-coloring device. Furthermore, if the two materials were ideally matched, so that at the applied voltage at which one is in its darkest state, the other is at its lightest state, this would then constitute an ideal complimentary-coloring, transmissive-mode electrochromic system.

In the present invention a complimentary polymer or "dual-polymer" electrochromic device is provided having electrodes and comprising an anodically-coloring conductive polymeric material, an electrolyte layer, and a cathodically coloring conductive polymeric material. As used herein, a "coloring conductive polymeric material" is said to be "anodically coloring" if application of a positive voltage to it causes it to transition to a colored or dark state, and "cathodically coloring" if application of a negative voltage causes it to transition to a colored or dark state. Moreover, cathodically and anodically coloring conductive polymeric materials comprise cathodically and anodically coloring polymers, respectively.

As used herein, the term "polymer" refers to the product of a polymerization reaction, and is inclusive of homopolymers, copolymers, terpolymers, etc.

As used herein, the term "homopolymer" is used with reference to a polymer resulting from the polymerization of a single monomer, i.e., a polymer consisting essentially of a single type of repeating unit.

As used herein, the term "copolymer" refers to polymers formed by the polymerization reaction of at least two different monomers and, moreover, the term copolymer is inclusive of random copolymers, block copolymers, graft copolymers, etc.

The cathodically coloring conductive polymeric material of the invention may comprise one or more polymers that comprise an unsubstituted or substituted derivative of 2,2-dibenzyl-3,4-propylene-dioxythiophene monomer. Preferably, when the 2,2-dibenzyl-3,4-propylene-dioxythiophene is substituted, the substitution may be located at the para position of the benzyl group, wherein the substituents at the benzyl moiety may be halo (e.g., chloro, bromo, iodo, fluoro), sulfonyl, nitro, amino or alkyl (e.g., n-propyl, iso-propyl, n-butyl, iso-butyl, n -pentyl, n-hexyl) substituents.

Preferably, the cathodically coloring polymer is a copolymer of monomers based on a 3,4-propylenedioxythiophene skeleton. Examples of such monomers include, but are not limited to, 2,2-bis(4-chlorobenzyl)-3,4-propylenedioxythiophene, 2,2-bis(4-bromobenzyl)-3,4-propylenedioxythiophene, 2,2-bis(4-nitrobenzyl)-3,4-propylenedioxythiophene, 2,2-bis(4-aminobenzyl)-3,4-propylenedioxythiophene and 2,2-dibenzyl-1,3-propylenedioxythiophene.

More preferably, the cathodically coloring conducting polymer is a copolymer of the monomers 2,2-dibenzyl-3,4-propylenedioxythiophene, 2,2-bis(4-chlorobenzyl)-3,4-propylenedioxythiophene, and 2,2-bis(4-bromobenzyl)-3,4-propylenedioxythiophene, taken in a molar ratio of about 1:1:1 to 50:1:1, reflecting the variation of the first monomer's proportion, and again from 50:1:1 to 50:7:1 and 1:1:1 to 1:7:1, reflecting the variation of the second monomer's proportion. More preferably, the above molar ratio is 50:1:1 to 3:1:1. More preferably still, the above molar ratio is 20:1:1 to 3:1:1. Most preferably, the above molar ratio is about 10:1:1. The electrochromic performance of electrochromic devices containing these copolymer systems is seen to be superior to that of devices having only pure polymers of these monomers.

Anodically coloring conducting polymeric materials of the invention may comprise one or more polymers or, more preferably, may be a copolymer of monomers known in the art which include but are not limited to poly(aromatic amine) polymers. Examples of such monomers include, but are not limited to, diphenyl amine, N,N'-diphenyl benzidine, 4-aminobiphenyl and aniline. The anodically coloring polymer is preferably a copolymer of monomers N,N'-diphenyl benzidine, diphenyl amine and 4-aminobiphenyl taken in a molar ratio of about 1:1:1 to 50:1:1, with electrochromic performance seen to be superior to that of the pure polymers of these monomers. Preferably, the above molar ratio is from about 1:1:1 to about 20:1:1. More preferably, the above molar ratio is from about 1:1:1 to about 9:1:1 and even more preferably, the above molar ratio is about 3:1:1 to 7:1:1. In an especially preferred embodiment, the above molar ratio is about 5:1:1.

Preferably, the cathodically and anodically coloring conductive polymers of the complimentary-polymer electrochromic device of the present invention are electrochromically and electrochemically matched. As used herein, the redox potentials of the cathodically coloring polymeric material and anodically coloring polymeric material in a 2-electrode electrochromic device are considered "substantially matched" when, at a given potential, the cathodically coloring polymeric material is fully oxidized and the anodically coloring polymeric material is fully reduced, and vice versa. More particularly, the cathodically and anodically coloring polymeric materials are considered "substantially matched" when the cathodically and anodically coloring polymeric materials both show at least about 85%, about 90%, or about 95% of their total charge transferred corresponding to their electrochromically relevant oxidation or reduction peaks, at a given potential, as determined by examining the area under the curve of the cathodically and anodically coloring polymeric material's individual voltammetric peaks.

Accordingly, where the cathodically and anodically coloring polymeric materials have substantially matched redox potentials, upon application of the (−) potential where the cathodically coloring polymeric material is at its darkest state, the anodically coloring polymeric material is at its lightest state; and, upon application of the (+) potential where the anodically coloring polymeric material is at its darkest state, the cathodically coloring polymeric material is at its lightest state.

Due to this good matching of the electrochemical redox potentials and the electrochromic properties of the complimentary polymers, the dual-polymer devices display electrochromic performance superior to that of the single-polymer devices as well as to prior art dual-polymer devices wherein either the cathodically-coloring or anodically-coloring polymer are different from the above listed polymers and are not electrochromically and electrochemically matched as described above. (Electrochromic performance is described by light/dark contrast, switching speed, cyclability, and related parameters).

In providing the dual-polymer devices of the present invention, the cathodically and anodically coloring polymeric materials may be composed of homopolymers. In preferred embodiments at least one of the cathodically coloring polymeric material and anodically coloring polymeric material may be composed of a copolymer. Most preferably, both the cathodically and anodically coloring polymeric materials are composed of copolymers. The anodically and cathodically coloring polymeric materials may be deposited on transparent conductive substrates which may form opposing electrodes in an electrochromic device with a thin layer (preferably a thin layer) of liquid, gel or solid electrolyte disposed between them. The device may further comprise a means (e.g. gasket) for sealing and containing said electrolyte within the device.

Additionally, methods are provided for assembling and preparing electrochromic devices which may utilize a deposition solution. The deposition solution used in the device and methods set forth may comprise (A) (1) for depositing a cathodically coloring polymer, (i) a 2,2-bis(benzyl)-3,4-propylenedioxythiophene derivative substituted at the para position of at least one benzyl group with a halo, sulfonyl, nitro or alkyl moiety and optionally (ii) 2,2-dibenzyl-3,4-propylenedioxythiophene; OR (2) for depositing an anodically coloring polymer, monomers N,N'-diphenyl benzidine, diphenyl amine and/or 4-aminobiphenyl; (b) a salt containing a counterion that is ultimately incorporated as the dopant in the polymer or copolymer deposited onto an electrode and (c) a solvent. The deposition solution may be obtained by combining a 2,2-bis(benzyl)-3,4-propylenedioxythiophene substituted at the para position of at least one benzyl group with a halo, sulfonyl, nitro or alkyl moiety and optionally 2,2-dibenzyl-3,4-propylenedioxythiophene with one or more salts in a solvent.

Salts that may be used in the deposition solution include but are not limited to $Na^+$, $Li^+$, $Et_4N^+$ as cations and poly(vinylsulfonate), sulfate, trifluoromethane sulfonate and poly(styrene sulfonate) as anions. Solvents that may be used include but are not limited to acetonitrile, N,N' dimethyl formamide (DMF), tetrahydrofuran (THF) and mixtures thereof. The polymer may be deposited from the deposition solution onto said transparent conductive substrate using a multiple potential sweep method, or a potential step (constant potential) method. More preferably for the cathodically coloring polymers, it may be deposited with a potential sweep method, with the potential from about 0.0 V to about +1.5V.

Cathodically-Coloring Polymer

The cathodically-coloring polymer comprises substituted and unsubstituted derivatives of poly(2,2-dibenzyl-3,4-propylenedioxythiophene) ("DiBz-PProDOT"). In particular reference to the substituted Dibenzyl-PProDOT, in a preferred embodiment, at least one benzyl moiety is substituted with an amino, nitro, halo, sulfonyl or alkyl group (e.g., propyl, isopropyl, n -butyl, iso-butyl, n-pentyl, n-hexyl). As used herein, "halo," may be defined as comprising fluoro, chloro, bromo and iodo substituents. In a particularly preferred embodiment, the para position of the benzyl group is substituted.

In a preferred embodiments, the cathodically-coloring polymers exhibit large electrochromic contrast and electrochemical and electrochromic compatibility with anodically-coloring polymers. DiBz-PProDOT polymers with dichloro- or other substituents at the para-position of each of the benzyl groups, may exhibit very significant improvement in electrochromic properties over their unsubstituted-dibenzyl-counterparts. In particular, with the substitution at the dibenzyl group, the polymer absorption may change such that it is more broad -band; additionally, the wavelength of highest absorption may also shift, potentially more towards the center of the visible spectral region (ca. 575 nm), and again, potentially, the switching voltages may be slightly lowered and made more symmetrical. Other possible changes of the substitution at the dibenzyl group could be a significant increase in the absorption, leading to a much higher light/dark contrast, and a shift in the redox potential, leading, potentially, to a much better match with anodically-coloring polymers such as poly(aromatic amines) in a dual-polymer device. Production of these polymers is achieved via electro-polymerization from the substituted-dibenzyl monomer, according to established conducting polymer electrochromics practice.

In another particular embodiment, the polymer may comprise a copolymer of derivatives of poly(2,2-dibenzyl-3,4-propylenedioxythiophene) substituted at the para position of the benzyl moiety. In particularly preferred embodiments, the monomer components may include 2,2-dibenzyl-3,4-propylenedioxythiophene, a derivative of 2,2-dibenzyl-3,4-propylenedioxythiophene substituted at the para position of the benzyl moiety with a chloro substituent and optionally a derivative of 2,2-dibenzyl-3,4-propylenedioxythiophene substituted at the para position of the benzyl moiety with a bromo substituent.

A particular cathodically coloring polymer composition of the invention is a copolymer of the monomers 2,2-dibenzyl-3,4-propylenedioxythiophene, 2,2-bis(4-chlorobenzyl)-3,4-propylenedioxythiophene, and 2,2-bis(4-bromo-benzyl)-3,4-propylenedioxythiophene, taken in a molar ratio of about 1:1:1 to 50:1:1, reflecting the variation of the first monomer's proportion, and again from 50:1:1 to 50:7:1 and 1:1:1 to 1:7:1, reflecting the variation of the second monomer's proportion. The electrochromic performance of electrochromic devices containing these copolymer systems is seen to be superior to that of devices having only pure polymers of these monomers. More preferably, the above molar ratio is 50:1:1 to 3:1:1. More preferably still, the above molar ratio is 20:1:1 to 3:1:1. Most preferably, the above molar ratio is about 10:1:1.

Synthesis of Monomer Precursors of High-Performance Cathodically Coloring Polymers The monomers used, particularly the derivatives set forth above may be obtained by providing a 2,2-dibenzyl-1,3-propanediol substituted at the 4-position (i.e., para position) of the benzyl group with the desired substituent (such as but not limited to the halo, alkyl, sulfonyl or nitro group). It is further noted that the p-bromo-substituted 2,2-bis(benzyl)-3,4-propylenedioxythiophene is particularly valuable as an intermediate in the further synthesis of monomer derivatives of 2,2-bis(benzyl)-3,4-propylenedioxythiophene with other substituents at the p-position of the benzyl group through common synthetic organic chemical techniques known to anyone skilled in the art. The 1,3-propanediol may be obtained by reducing a 2,2-dibenzyl-malonate substituted at the 4 position of the benzyl group with the desired substituent (such as but not limited to the halo, alkyl, sulfonyl or nitro group). Examples of various malonates that may be used and methods of synthesis are set forth in the text below and in the EXAMPLES.

The 2,2-bis(benzyl)-1,3-propanediol substituted at the 4 position of the benzyl group with the desired substituent (such as but not limited to the halo, sulfonyl or nitro group) is reacted with 1,3-dimethoxythiophene in a transesterification reaction facilitated by, for example, p-toluene sulfonic acid to yield the monomer, bis(4-substituted-benzyl)-3,4-propylenedioxythiophene.

Figure 3:
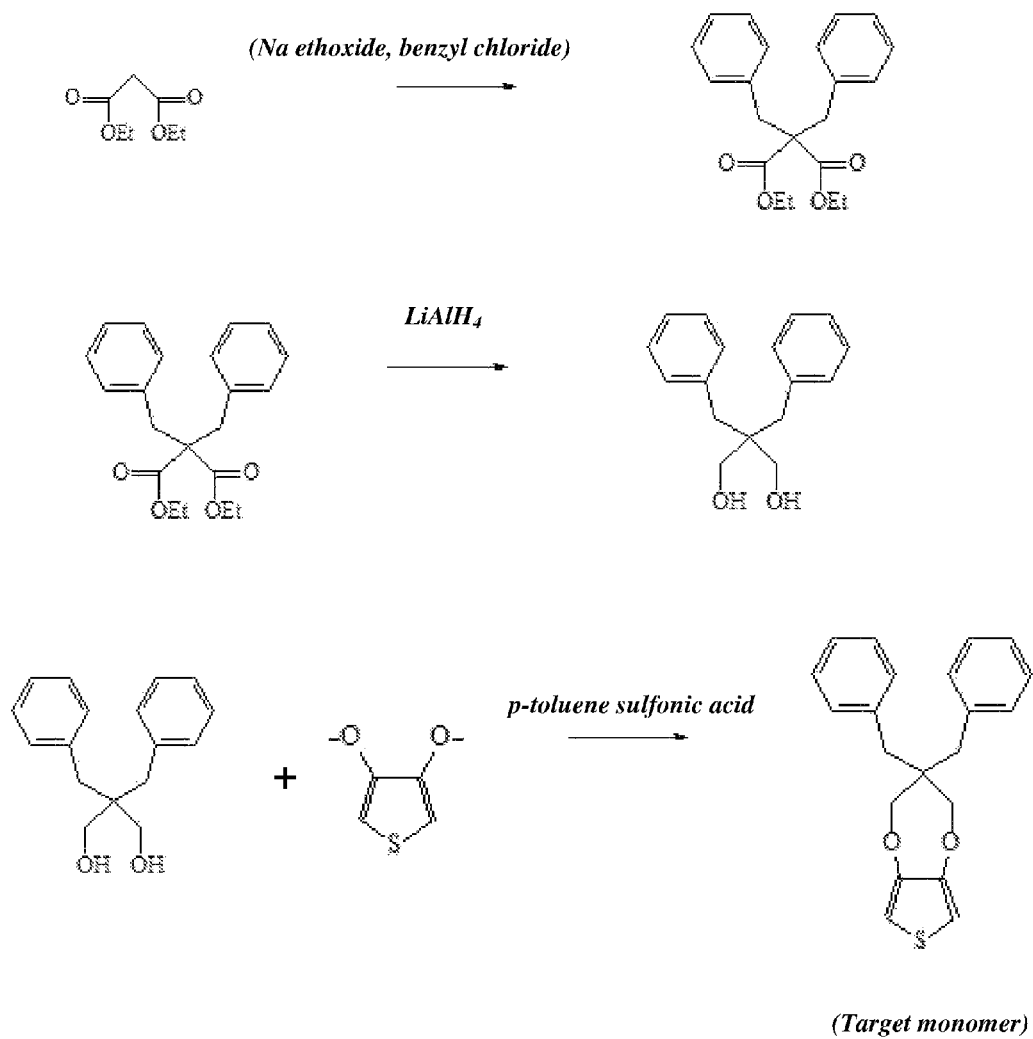
FIG. 3 shows the synthetic scheme as used by Krishnamoorthy et al. for synthesis of the monomer 2,2-dibenzyl-ProDOT (2,2-dibenzyl-propylene-dioxythiophene, "Bz-ProDOT").

This synthetic task is not entirely trivial. Krishnamoorthy et al. synthesized dibenzyl -PProDOT using a transesterification reaction between 3,4-dimethoxy-thiophene and 2,2-dibenzyl-propane-1,3-diol (as seen in the scheme in FIG. 3). The latter in turn was synthesized starting with diethyl malonate and reacting it with benzyl chloride to yield 2,2-dibenzyl -diethyl malonate using a strong base (sodium ethoxide in ethanol medium). The 2,2-dibenzyl-diethyl malonate was in turn reduced to yield the 2,2-dibenzyl-propane-1,3-diol using a standard lithium-aluminum-hydride reduction.

While diethyl malonate may react in a straightforward manner with benzyl chloride, facilitated by the strong base sodium ethoxide, the same cannot be said for the p-substituted benzyl chlorides, e.g. the p-chloro-substituted benzyl chloride. In fact, the reaction in sodium ethoxide medium fails, as does the reaction with other base media commonly used in organic synthesis, such as triethyl amine and di-isopropylethyl amine (see COMPARATIVE EXAMPLES). It thus appears that the availability of the para position on the benzyl rings is required for the success of this reaction with common organic bases, and when it is blocked, the reaction fails. This is illustrated in a comparison of syntheses of the monomer 2,2-bis(4-chlorobenzyl)-3,4-propylenedioxythiophene) ("Cl-Bz-ProDOT) described in EXAMPLE 1 (the successful synthesis using the base and reaction conditions of choice, involving steps through the intermediates diethyl-bis(4-Cl-benzyl) malonate and 2,2-bis(4-chlorobenzyl)-propanediol) versus COMPARATIVE EXAMPLES 2, 3 and 4 (unsuccessful syntheses using bases commonly used in organic synthesis for synthesis of the 1st intermediate above, diethyl-bis(4-Cl-benzyl) malonate).

Another subject of the present invention, therefore, is the successful synthesis of the precursors required to synthesize the p-dichloro-, p-dibromo and p-dinitro-substituted dibenzyl PPro-DOT electrochromic polymers, specifically, 2,2-bis(4-chloro-benzyl)-1,3-propanediol, 2,2-bis(4-bromo-benzyl)-1,3-propanediol, and 2,2-bis(4-nitro-benzyl)-1,3-propanediol. Typical syntheses are described in EXAMPLES 1, 5 and 6.

Synthesis of the monomer, 2,2'-(bis-4-nitrobenzyl)-3,4-propylenedioxythiophene ("$NO^2$-Bz-ProDOT"), i.e. the nitro-substituted analog of the chloro-substituted monomer described above, starts with 4-nitrobenzyl bromide and includes a series of steps which involve use of protective groups, as described at length in EXAMPLE 6, which also reference the relevant reaction schemes represented in the FIGURES.

EXAMPLE 8 describes a typical electrochemical deposition (i.e., polymerization) of the polymer, poly(2,2-bis(4-chloro-benzyl)-3,4-propylenedioxythiophene) ("poly(Cl-Bz-ProDOT)") from monomer solution.

The polymer is preferably deposited from a nonaqueous monomer solution. A potential sweep method is preferably used. A potentiostatic (constant potential) method yields poorly formed, inhomogeneous polymer films with poor electrochromic performance and with a tendency to crack. More preferably, a multiple potential sweep method is used with total charge during deposition controlled carefully. The potential is swept from about 0.0 V to +1.5 V (vs. Pt quasi-reference). More preferably, the potential sweep rate is 10-25 mV/s with potential step size between 2 and 7 mV, and the total charge during deposition is 7.5 to 12.5 mC/cm$^2$. Polymer films deposited using these parameters have a blue-violet coloration, are extremely homogeneous and uniform, and yield a % T, at 575 nm (the approximate wavelength of maximum absorption for this polymer), of 45% to 50%. They display the most optimal electrochromic performance in devices, as characterized by light/dark contrast (Delta % T at 575 nm), switching time, cyclability and durability.

In preferred embodiments of the invention, electrochemical deposition of the cathodically coloring polymer is provided with a potential sweep method rather than a potentiostatic method; the latter yields poor films with poor electrochromic performance. During such deposition, the potential is swept from about 0.0 V to +1.5 V (vs. Pt quasi-reference), a preferred scan rate is 2 mV/s to 50 mV/s and a preferred potential step size from 1 mV to 10 mV. A more preferred scan rate is 10-20 mV/s, and a more preferred potential step size is between 2 and 4 mV; a preferred total charge is 11 to 19 mC/cm$^2$ and a preferred % T of the film as deposited at 575 nm is 41% to 55%. Highly uniform, homogeneous polymer films with a dark blue/violet coloration are obtained. A typical such electrochemical deposition is described in EXAMPLE 11. Based on established principles of electrochemical polymerization of conducting polymers (see Chandrasekhar, 1999, Chapters 1-3), and without being confined to any particular theory of operation, it is highly likely that the polymer chain in this copolymer contains random units of the three monomers in the proportions noted above (e.g. 5:1:1) such that the extended conjugation in the polymer chain has properties corresponding to contributions from the strongly electron-withdrawing chloro-substituent and the less electron-withdrawing bromo-substituent, along with the "neutral" unsubstituted monomer. Additionally, the larger substituents (benzyl, chloro-benzyl, bromo-benzyl) impose greater structural order (reflected, e.g. in less cross-linking) and thus further improve the extended conjugation of the resulting conducting polymer. This unique extended conjugation and unique stereochemistry leads to improved electrochromic properties, as described further below.

EXAMPLES 8 and 10 describe the electrochemical depositions of other cathodically-coloring polymers. COMPARATIVE EXAMPLE 9 describes such deposition using a potentiostatic (constant potential) method; this yields poorly formed, non-uniform polymer susceptible to cracking and displaying much poorer electrochromic properties.

Anodically Coloring Polymer

The anodically coloring polymers used in the electrochromic device may be those materials known in the art and may include but are not limited to: poly(pyrrole); the structurally related poly(aromatic amine) series comprising poly(diphenyl amine), poly(4-amino-biphenyl) (Guay et al., 1989) and poly(aniline); poly(N,N'-diphenyl benzidine) (Suzuki et al., 1989); poly(phenylene); poly(phenylene vinylene); poly(alkylene vinylene); poly(amino quinoline).

A preferred composition for the anodically coloring polymer is a copolymer of N,N'-diphenyl benzidine, diphenyl amine and 4-amino-biphenyl, in a ratio of about 1:1:1 to 50:1:1 to, with electrochromic performance seen to be superior to that of the pure (i.e. non-copolymer) polymers of these monomers. More preferably, the above molar ratio is from about 1:1:1 to about 20:1:1 and even more preferably, the above molar ratio is about 10:1:1 to 20:1:1. In other preferred embodiments, the above molar ratio is about 3:1:1 to 9:1:1, and even more preferably, the above molar ratio is about 4:1:1 to 7:1:1. In a specifically preferred embodiment, the above molar ratio is about 5:1:1.

As for the cathodically-coloring copolymers described above, established principles of electrochemical polymerization of conducting polymers (see Chandrasekhar, 1999, Chapters 1-3) indicate that it is likely that the polymer chain in this copolymer contains random units of the three monomers in the proportions used. The properties of the copolymer resulting therefrom are thus a composite of the contributions to the extended conjugation of the individual monomers. Additionally, the presence of the three monomers, and most especially the N,N'-diphenyl substituted monomer, is expected to introduce greater structural regularity in the resulting copolymer. These unique characteristics of the copolymer lead to improved electrochromic properties, as described further below. A typical electrodeposition of an anodically-coloring copolymer is described in EXAMPLE 12.

Another aspect addressed in the present invention is the improvement of procedures for preparation of monomer solutions of anodically coloring polymers described in the prior art, which were found in extensive studies to either not work or work very poorly. An example of this is the preparation of the monomer solution of the N,N'-diphenyl benzidine, as described in the work of Suzuki et al. (1989). It was found in the repetition of their procedures for preparation of solutions of this monomer in N,N'-dimethyl formamide (DMF) and acetonitrile solvents (solutions to be subsequently used in electrochemical polymerization of the corresponding polymer, poly(N,N'-diphenyl benzidine)), that: (1) In the case of this monomer solution in DMF solvent, no polymer film was formed on a variety of substrates using a wide variety of chemical and electrochemical deposition (polymerization) conditions (see COMPARATIVE EXAMPLE 13). (2) And in the case of the monomer solution in acetonitrile solvent, the solubility of the monomer was so poor and the monomer solution obtained in acetonitrile so dilute that electrochemical deposition (polymerization) of even very thin films of polymer took more than 4 hours and in some cases even longer. Thus, even though in the case of DMF solvent, the monomer had very high solubility, no polymer deposited on ITO substrates using a very wide variety of potential sweep and potential step methods. And again, in the case of acetonitrile solvent, the solubility of the monomer was so poor that an extremely dilute monomer solution, of concentration <0.1 mM, was obtained in acetonitrile. As a result, the potentiostatic electro-polymerization on ITO substrates took an inordinately took an inordinately long time and potential sweep polymerization also yielded very thin films even over several hundred sweeps. These unsuccessful studies are described in COMPARATIVE EXAMPLE 13.

A modified procedure with DMF and acetonitrile solvents of a particular proportion worked well to dissolve this monomer as well as to yield the corresponding polymer film of acceptable thickness on ITO substrates in a times less than 40 minutes. These studies are described in COMPARATIVE EXAMPLE 13 In particular, it was found that the optimal volume ratio of acetonitrile to DMF was in the region of 6:1 (v/v %). Ratios of 7:1 or higher were found to yield very thin polymer films over very long (>2 h) periods of deposition, whilst ratios of 5:1 or lower were found not to yield any polymer films or extremely poor films that showed very poor adhesion to the ITO substrates and could be simply shaken off in acetonitrile solvent. Thus, the ca. 6:1 ratio of DMF:acetonitrile was an unexpected result in that it yielded viable films of polymer, both for the monomer N,N'-diphenyl benzidine alone, and its copolymers with other aromatic amine monomers.

Substrate

Preferred substrates are ITO (indium tin oxide) on a chemically inert plastic such as poly(ethylene terephthalate) (PET), i.e. ITO/Mylar®, although any other conductive, transparent substrate may be used, such as: ITO/glass; doped tin oxide on glass or plastic; very thin (<60 nm) Au on plastic or glass; "NESA" glass; and a more recently studied substrate, carbon nanotubes on plastic or glass. For the preferred substrate, ITO/Mylar, the preferred surface resistivity is <60 Ohms/square (dimensionless units).

Deposition of Polymers/Copolymers on the Substrate

The polymer is preferably deposited from a nonaqueous monomer solution. A potential sweep method is preferably used in the case of the cathodically coloring polymers and a potential step method is preferably used in the case of the anodically coloring polymers addressed here. EXAMPLES 8 and 10 describe the electrochemical depositions of other cathodically -coloring polymers. COMPARATIVE EXAMPLE 9 describes such deposition of the cathodically coloring polymers using a potentiostatic (constant potential) method; this yields poorly formed, non -uniform polymer susceptible to cracking and displaying much poorer electrochromic properties.

Thus, more preferably, in the case of the cathodically coloring polymers addressed here, a multiple potential sweep method is used with total charge during deposition controlled carefully. The potential is swept from about 0.0 V to +1.5 V (vs. Pt quasi-reference). In a particular embodiment, the potential sweep rate is 10-25 mV/s with potential step size between 2 and 7 mV, and the total charge during deposition is 7.5 to 12.5 mC/cm$^2$. Polymer films deposited using these parameters have a blue-violet coloration, are extremely homogeneous and uniform, and yield a % T, at 575 nm (the approximate wavelength of maximum absorption for this polymer), of 45% to 50%. They display the most optimal electrochromic performance in devices, as characterized by light/dark contrast (Delta % T at 575 nm), switching time, cyclability and durability.

Similar procedures may be used to deposit a copolymer. During such deposition, the potential is swept from about 0.0 V to +1.5 V (vs. Pt quasi-reference), a preferred scan rate is 2 mV/s to 50 mV/s and a preferred potential step size from 1 mV to 10 mV. A more preferred scan rate is 10-20 mV/s, and a more preferred potential step size is between 2 and 4 mV; a preferred total charge is 11 to 19 mC/cm$^2$ and a preferred % T of the film as deposited at 575 nm is 41% to 55%. Highly uniform, homogeneous polymer films with a dark blue/violet coloration are obtained. A typical such electrochemical deposition is described in EXAMPLE 11. Based on established principles of electrochemical polymerization of conducting polymers (see Chandrasekhar, 1999, Chapters 1-3), and without being confined to any particular theory of operation, it is likely that the polymer chain in this copolymer contains random units of the three monomers in the proportions noted above (e.g. 5:1:1) such that the extended conjugation in the polymer chain has properties corresponding to contributions from the strongly electron -withdrawing chloro-substituent and the strongly electron-donating amino-substituent, along with the "neutral" unsubstituted monomer. Additionally, the larger substituents (benzyl, chloro-benzyl, nitro-benzyl) impose greater structural order (reflected, e.g. in less cross-linking) and thus further improve the extended conjugation of the resulting conducting polymer. This unique extended conjugation and unique stereochemistry leads to improved electrochromic properties, as described further below.

Electrochromic Device, Including Assembly Thereof and Electrolytes

Figure 1:
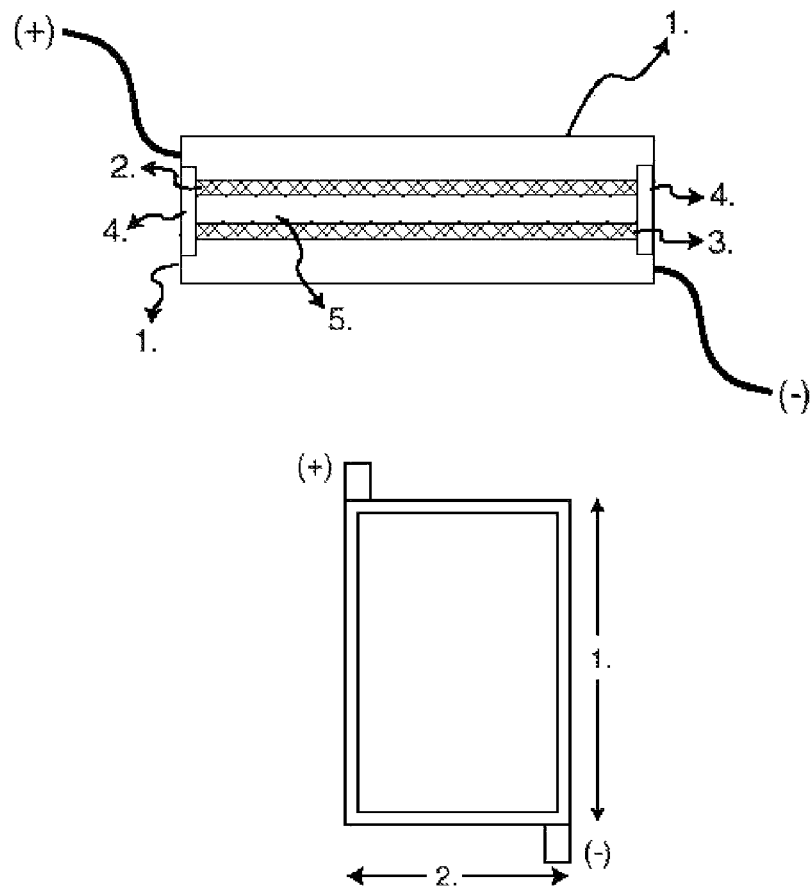
FIG. 1 shows cross-sectional and top views of the complimentary polymer ("dual-polymer") electrochromic device according to the present invention.

Electrochromic devices are assembled according to the schematic of FIG. 1. Typical assemblies are described in EXAMPLE 14 and COMPARATIVE EXAMPLES 15-17.

For the electrolyte for the devices, a gel electrolyte is preferred. A procedure for synthesis of a preferred electrolyte, adapted from electrolytes presented in the prior art, is described in EXAMPLE 14. A preferred electrolyte uses a polymer such as poly(methyl methacrylate) (PMMA) or poly(ethyl methacrylate) (PEMA) as a matrix, appropriate salts such as Li trifluoromethane sulfonate (Li triflate) and LiBF$_4$, and plasticizers and/or further solvating agents such as propylene carbonate, which is an organic solvent (typically used in Li battery electrolytes) with a very high b.p., 240° C. Once set, the gel electrolyte resembles a hard but flexible, rubbery plastic.

As seen in the schematic in FIG. 1, the components of the electrochromic devices comprise the two conducting polymer electrodes (with cathodically- and anodically-coloring polymers, respectively), the electrolyte and gaskets for sealing and for containing the electrolyte. The electrolyte is applied to both polymer electrodes as a very thin layer using a doctor-blade technique. Overnight setting yields a complete device, which may then be optionally sealed with additional edge-sealants.

EXAMPLE 14 describes in detail the assembly of a typical dual-polymer device. In this case, the cathodically-coloring polymer is a copolymer of 2,2-(bis-4-chloro-benzyl) -3,4-propylenedioxythiophene, 2,2-(bis-4-bromo-benzyl)-3,4-propylenedioxythiophene and 2,2-dibenzyl-3,4-propylenedioxythiophene and the anodically-coloring polymer is a copolymer of N,N'-diphenyl benzidine, diphenyl amine and 4-amino-biphenyl. COMPARATIVE EXAMPLE 15 describes the assembly of dual-polymer electrochromic device comprising poly(2,2-(bis-4-chloro-benzyl)-3,4-propylenedioxythiophene) ("poly(Cl-Bz-ProDOT)") as the cathodically coloring polymer and a copolymer of N,N'-diphenyl benzidine, diphenyl amine and 4-amino -biphenyl as the anodically coloring polymer. COMPARATIVE EXAMPLE 16 describes the assembly of dual-polymer electrochromic device comprising the prior art polymer, poly(isothianaphthene) (PITN), as the cathodically coloring polymer and a copolymer of N,N'-diphenyl benzidine, diphenyl amine and 4-amino-biphenyl as the anodically coloring polymer. COMPARATIVE EXAMPLE 17 describes the assembly of single-polymer electrochromic device comprising poly(N,N'-diphenyl benzidine) as the anodically coloring polymer.

Electrochromic Performance of Dual-Polymer and Single-Polymer, Including Copolymer Devices A known cathodically-coloring polymer, poly(isothianaphthene) (PITN), serves as a useful reference and benchmark in the comparison of dual-polymer devices. The redox potentials of this polymer, PITN, are somewhat poorly matched to those of virtually all anodically-coloring polymers, and particularly poorly matched to those of poly (aromatic amines) such as poly(diphenyl amine), poly(4-amino-biphenyl) and poly(N,N'-diphenyl benzidine). This is further confirmed in the cyclic voltammogram shown in FIG. 8, which shows cyclic voltammograms of a device as assembled in COMPARATIVE EXAMPLE 16, i.e. with PITN as the cathodically-coloring polymer and a copolymer of N,N'-diphenyl benzidine, diphenyl amine and 4-amino-biphenyl as the anodically-coloring polymer, between the voltages corresponding to its extreme light and dark states. The voltammogram is seen to have poorly defined oxidation peaks. More telling is the poor electrochromic performance embodied in FIG. 9, which shows the UV-Vis-NIR spectra of this device in its extreme light and dark states; the poor contrast (Delta % T) is clearly seen. Nevertheless, being a dual-polymer device, this device shows a switching time <5 s, and cyclability, >2000 cycles.

Another useful comparison is obtained from the performance of the device as assembled in COMPARATIVE EXAMPLE 17, i.e. a single-polymer electrochromic device comprising poly(N,N'-diphenyl benzidine) as the anodically coloring polymer. Its extreme light/dark state electrochromic performance, seen in FIG. 10, shows a Delta % T at the wavelength of maximum absorption of about 40%, which may be considered fair to good. However, the device shows a rather poor switching time, ca. 15 to 20 s, and starts to degrade significantly after about 1000 light/dark cycles. These performance data substantiate the view that single-polymer devices show poorer performance than dual-polymer devices.

A relative comparison of the superior electrochromic performance of the electrochromic devices and systems of the present invention can be seen in the data in FIGS. 11-13. FIG. 11 shows the UV-Vis-NIR spectra in the extreme light/dark states of the dual-polymer device assembled according to COMPARATIVE EXAMPLE 15, i.e. with poly(2,2-(bis-4-chloro-benzyl)-3,4-propylenedioxythiophene) ("Poly(Cl-Bz-ProDOT)") as the cathodically coloring polymer and a copolymer of N,N'-diphenyl benzidine, diphenyl amine and 4-amino-biphenyl as the anodically coloring polymer, along with the dual-polymer device assembled according to EXAMPLE 14, i.e. with a copolymer of 2,2-(bis-4-chloro-benzyl)-3,4-propylenedioxythiophene, 2,2-(bis-4-bromo-benzyl)-3,4-propylenedioxythiophene and 2,2-dibenzyl-3,4-propylenedioxythiophen] as the cathodically coloring polymer and a copolymer of N,N'-diphenyl benzidine, diphenyl amine and 4-amino-biphenyl as the anodically coloring polymer. It is noted that the thicknesses of the copolymers in both devices were prepared to be nearly identical, to enable a better direct comparison. It is seen, firstly, that the single-cathodically-coloring -polymer device shows a very large light/dark contrast, about Delta % T 55% at 575 nm (the approximate wavelength of maximum absorption). Secondly, it is seen that the copolymer-cathodically-coloring -polymer device shows significantly increased contrast, Delta % T about 60% at 575 nm, and a more broad-band response in the light state, although the dark state is nearly identical to that of the single-polymer device. FIG. 12 shows switching time data for the same devices. Although the switching times appear nearly identical for the two devices, the copolymer devices again show a larger light/dark contrast.

The fact that the cathodically-coloring and anodically-coloring copolymers of the device of EXAMPLE 14 are extremely well matched electrochemically, i.e. in terms of their redox potentials, is clearly seen from the relevant electrochemical, i.e. cyclic voltammetric data, as shown in FIG. 13. A key indicator of this is that the currents observed in the redox of the single-polymer devices are much smaller than those of the composite, dual-polymer device, clearly seen in the figure. Since, in the case of the dual-polymer device, oxidation or reduction at one electrode is accompanied by a companion, highly reversible opposite process, i.e. reduction or oxidation, at the other electrode, redox of each polymer is much more facile; there is then a concomitant, very significant increase in the observed current. In essence, more of the polymer is electroactive and switching in the case of the dual polymer device as compared to the single polymer devices.

Furthermore, the fact that the cathodically-coloring copolymer, i.e. the copolymer of 2,2-bis(4-chloro-benzyl)-3,4-propylenedioxythiophene, 2,2-bis(4-bromo -benzyl)-3,4-propylenedioxythiophene and 2,2-dibenzyl-3,4-propylenedioxythiophene, constitutes a better electrochemical match for the anodically-coloring copolymer (the copolymer of N,N'-diphenyl benzidine, diphenyl amine and 4-amino-biphenyl) than the individual polymer, poly(2,2-bis(4-chloro-benzyl)-3,4-propylenedioxythiophene) (P(Cl-Bz-ProDOT)), alone is seen in the cyclic voltammetric data of FIG. 14. Here, it is seen that, for polymer films having nearly identical charge during deposition (and thus also expected to have nearly identical thickness), the voltammogram for the copolymer device is more well defined and has significantly higher currents than that for the P(Cl-Bz-ProDOT)-only device. Again, this implies that more of the polymer in the former case is electroactive and switching.

Another advantage possessed by the dual-copolymer devices of the present invention is that the light/dark spectra "window" can be shifted up or down with ease. That is to say, if, e.g., the dark and light state transmissions (% T) of a device are 8% and 60% respectively (at 575 nm), then with appropriate adjustment of the total charge during deposition of the polymers, i.e. their thickness, the dark and light state % T can be shifted, e.g., to 2% and 54%, in a nearly linear fashion. This is seen in the light/dark data in FIG. 15. In this figure, although the dark state shows a % T of about 0% in approximately the 550 nm to 630 nm region, it is important to note that this is somewhat deceptive in terms of the visibility through such a device. Such a device just appears tinted, and is still easily seen through; there is no impediment to visibility whatsoever, due to the fact that there is significant transmission at the other visible wavelengths.

Regarding certain specific embodiments of the present invention, the present invention encompasses windows, mirrors, flat panel displays, visors, glasses, and camouflage, comprising the complimentary electrochromic devices of the present invention.

The following examples describe the invention in further detail. These examples are provided for illustrative purposes only, and should in no way be considered as limiting the invention.

EXAMPLES

Example 1

Typical Synthesis of Monomer, 2,2-(bis-4-chlorobenzyl)-3,4-propylenedioxythiophene ("3,3-Bis(4-chlorobenzyl)-3,4-dihydro-2H-thieno[3,4-b][1,4]-dioxepine") ("Cl-Bz-ProDOT")

a. Synthesis of initial intermediate, diethyl bis(4-chlorobenzyl) malonate (Scheme, FIG. 4): The synthesis was carried out under inert atmosphere with dry Argon gas utilizing a balloon apparatus. To a 250 mL round bottom flask was added 11.2 g (0.0545 mol) of 4-chlorobenzyl bromide, 17.0 g (0.123 mol) of potassium carbonate and 100 mL of anhydrous DMF. The neck of the flask was closed with a rubber septum and the flask was purged with Ar. A rubber balloon/needle apparatus was filled with Ar and inserted into the septum. After the balloon was attached, 3.3 mL (0.022 mol) of diethyl malonate was inserted via a syringe and the flask was heated to 100° C. for 16 h. The flask was cooled to room temperature and the reaction mixture was poured into 200 mL of water. The product was extracted with diethyl ether. The ether layer was washed three times with 100 mL of water and once with 100 mL of brine. The ether layer was dried with $MgSO_4$ and filtered. Solvent was removed in vacuo. The residue was recrystallized from hexanes to give 2.87 g (32%). Identity of intermediates and products were confirmed via TLC and NMR (proton, $^{13}C$).

b. Alternate synthesis of initial intermediate, diethyl bis (4-chloro-benzyl) malonate (Scheme, FIG. 4): The synthesis was carried out under inert atmosphere with dry Argon gas utilizing a balloon apparatus. To a 250 mL round bottom flask was added 8.8 mL (0.0746 mol) of 4-chlorobenzyl chloride, 17.0 g (0.123 mol) of potassium carbonate, 0.59 g tetrabutylammonium triflate (0.00150 mol) and 80 mL of anhydrous toluene. The mixture was heated to reflux for 16 h. The solution was cooled to room temperature. The insoluble salts were filtered and washed thoroughly with dichloromethane. The solvents were removed in vacuo. Column chromatography was performed on the residue with a silica gel column (25 cm×2.5 cm) using a gradient of pure hexanes to 20% (v/v) dichloromethane in hexanes as the eluent. 3.3 g (11%) of the desired material was obtained. Identity of intermediates and products were confirmed via TLC and NMR (proton, $^{13}C$)

c. Reduction of diethyl bis-(4-chlorobenzyl) malonate to 2,2-bis(4-chloro -benzyl)-1,3-propandiol (Scheme, FIG. 4): To a 250 mL three neck round bottom flask was added 1.92 g (50.5 mmol) of lithium aluminum hydride. The flask was purged with Ar and cooled to 0° C. 20 mL of anhydrous THF was added to the flask. To this flask was added 3.3 g (8.06 mmol) of diethyl bis(4-chlorobenzyl) malonate dissolved in 15 mL THF. The addition was done slowly via a syringe at approximately a dropwise addition pace. The mixture was stirred overnight. After stirring, the mixture was cooled to 0° C. and 1.92 mL of de-ionized water was added very slowly. After this addition 1.92 mL of 15% sodium hydroxide was added then 5.76 mL of de-ionized water. The mixture was stirred for 1 h. The solid was filtered off and thoroughly washed with diethyl ether. The solvent was removed in vacuo. Column chromatography was performed on the residue with a silica gel column (25 cm×2.5 cm) using a gradient of pure hexanes to 60% (v/v) ethyl acetate in hexanes as the eluent. 2.58 g (98%) of the desired material was obtained. IR, $^1HNMR$, $^{13}C$ NMR in addition to TLC were used to confirm identity of the product.

d. Alternate reduction of diethyl bis-(4-chlorobenzyl) malonate to 2,2-bis(4-chloro-benzyl)-1,3-propandiol (Scheme, FIG. 4): To a 50 mL round bottom flask was added 2.87 g (7.01 mmol) of diethyl bis(4-chlorobenzyl) malonate. The neck of the flask was closed with a rubber septum and the flask was purged with Ar. A rubber balloon/needle apparatus was filled with Ar and inserted into the septum. To the flask was added 15 mL (30 mmol) of 2.0 M $LiBH_4$. The flask was heated to 50° C. overnight. It was then cooled to 0° C. and 12 mL of a saturated solution of $(NH_4)_2SO_4$ was slowly added to the flask. The solution was then poured into a 250 mL separatory funnel and the product was extracted with ethyl acetate. The organic layer was washed twice with 100 mL of water and once with brine. The solution was dried with $MgSO_4$. Solvent was removed in vacuo to give 1.65 g (72%) of the alcohol. IR, $^1HNMR$, $^{13}CNMR$ in addition to TLC were used to confirm identity of the product. This material was used without purification in next step.

e. Reaction of 2,2-bis(4-chloro-benzyl)-1,3-propanediol with 3,4-dimethoxythiophene to produce the final monomer, 2,2-(bis-4-chlorobenzyl)-3,4-propylenedioxythiophene (("3, 3-Bis(4-chlorobenzyl)-3,4-dihydro-2H -thieno[3,4-b][1,4]-dioxepine" "Cl-Bz-ProDOT") (Scheme FIG. 4): To a 500 mL round bottom flask was added 1.65 g (5.07 mmol) 2,2 bis(4-chlorobenzyl)-1,3 propanediol, 0.200 g (1.05 mmol) p-toluenesulfonic acid monohydrate and 100 mL of toluene. The neck of the flask was closed with a rubber septum and the flask was purged with $N_2$. A rubber balloon/needle apparatus was filled with $N_2$ and inserted into the septum. To the mixture was added 0.49 mL (4.11 mmol) of 3,4-dimethoxythiophene and the flask was heated to 80° C. for 1 d (~17 h). The flask was cooled to room temperature and the solvent was removed in vacuo. Column chromatography was performed on the residue with a silica gel column (25 cm×2.5 cm) using a gradient of pure hexanes to 30% (v/v) dichloromethane in hexanes as the eluent. 1.03 g (50%) of the desired material was obtained. IR, $^1HNMR$, $^{13}CNMR$ in addition to TLC were used to confirm identity of the product.

Comparative Example 2

Alternative Syntheses of Monomer, 2,2-(bis-4-chlorobenzyl)-3,4-propylenedioxythiophene ("Cl-Bz-ProDOT")

The synthesis of diethyl bis(4-chloro-benzyl) malonate was carried out in a manner substantially identical to that described in EXAMPLE 1, Step a. above, except that the proportionate molarity of triethyl amine was substituted for the $K_2CO_3$. The reaction was observed to be extremely slow and no product was obtained over a period of 72 hours.

Comparative Example 3

Alternative Syntheses of Monomer, 2,2-(bis-4-chlorobenzyl)-3,4-propylenedioxythiophene ("Cl-Bz-ProDOT")

The synthesis of diethyl bis(4-chloro-benzyl) malonate was carried out in a manner substantially identical to that described in EXAMPLE 1, Step a. above, except that the proportionate molarity of di-isopropyl ethyl amine was substituted for the $K_2CO_3$. The reaction was observed to be extremely slow and no product was obtained over a period of 72 hours.

Comparative Example 4

Alternative Syntheses of Monomer, 2,2-(bis-4-chlorobenzyl)-3,4-propylenedioxythiophene ("Cl-Bz-ProDOT")

The synthesis of diethyl bis(4-chloro-benzyl) malonate was carried out in a manner substantially identical to that described in EXAMPLE 1, Step a. above, except that the proportionate molar quantity of 0.9 M solution of Na ethoxide in ethanol was substituted for the $K_2CO_3$. No reaction was observed to occur and no product was obtained over a period of 72 hours.

Example 5

Figure 5:
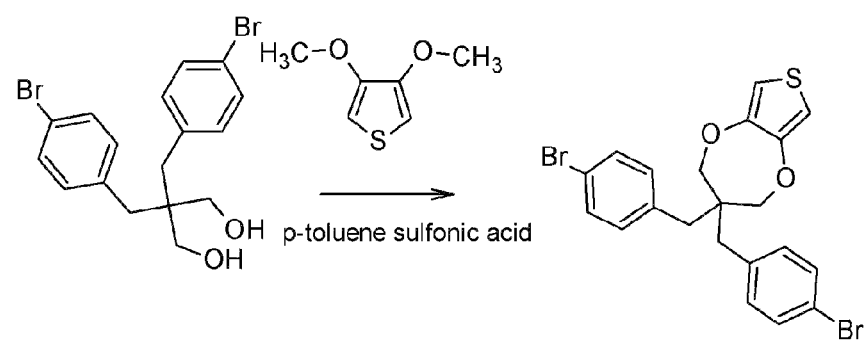
FIG. 5 shows the synthetic scheme for synthesis of the monomer 2,2-(bis-4-bromobenzyl)-3,4-propylenedioxythiophene (also called "3,3-Bis(4-bromobenzyl)-3,4-dihydro-2H-thieno[3,4-b][1,4]-dioxepine" or "Br-Bz-ProDOT"), according to the present invention.

Typical Synthesis of Monomer, 2,2-(bis-4-bromobenzyl)-3,4-propylenedioxythiophene ("3,3-Bis(4-bromobenzyl)-3,4-dihydro-2H-thieno[3,4-b][1,4]-dioxepine") ("Br-Bz-ProDOT")

a. Synthesis of initial intermediate, diethyl bis(4-bromobenzyl) malonate (Scheme, FIG. 5): To a 250 mL round bottom flask was added 8.63 g (0.0345 mol) of 4-bromobenzyl bromide, 17.0 g (0.123 mol) of potassium carbonate and 100 mL of anhydrous DMF. The neck of the flask was closed with a rubber septum and the flask was purged with Ar. A rubber balloon/needle apparatus was filled with Ar and inserted into the septum. After the balloon was attached, 2.2 mL (0.014 mol) of diethyl malonate was inserted via a syringe and the flask was heated to 100° C. for 16 h. The flask was cooled to room temperature and the reaction mixture was poured into 200 mL of water. The product was extracted with diethyl ether. The ether layer was washed three times with 100 mL of half brine and once with 100 mL of brine. The ether layer was dried with $MgSO_4$ and filtered. Solvent was removed in vacuo. The residue was recrystallized from hexanes to give 1.42 g (20%). IR, $^1$HNMR, $^{13}$CNMR in addition to TLC were used to confirm identity of the product.

b. Synthesis of intermediate, 2,2 Bis(4-bromobenzyl)-1,3 propanediol (Scheme, FIG. 5): To a 50 mL round bottom flask was added 1.42 g (2.85 mmol) of diethyl bis(4-bromobenzyl) malonate. The neck of the flask was closed with a rubber septum and the flask was purged with Ar. A rubber balloon/needle apparatus was filled with Ar and inserted into the septum. To the flask was added 15 mL (30 mmol) of 2.0 M $LiBH_4$. The flask was heated to 50° C. overnight. It was then cooled to 0° C. and 12 mL of a saturated solution of $(NH_4)_2SO_4$ was slowly added to the flask. An additional 50 mL of water was added to the mixture and the solution was then poured into a 250 mL separatory funnel. The product was extracted with ethyl acetate and the organic layer was washed twice with 100 mL of water and once with brine. The solution was dried with $MgSO_4$. Solvent was removed in vacuo to give 1.00 g (85%) of the alcohol. This material was used without purification in next step. IR, $^1$HNMR, $^{13}$CNMR in addition to TLC were used to confirm identity of the product.

c. Reaction of 2,2-bis(4-bromo-benzyl)-1,3-propanediol with 3,4-dimethoxythiophene to produce the final monomer, 2,2-(bis-4-bromobenzyl)-3,4-propylenedioxythiophene (("3,3-Bis(4-bromobenzyl)-3,4-dihydro-2H-thieno[3,4-b][1,4]-dioxepine" "Br-Bz-ProDOT") (Scheme, FIG. 5): To a 200 mL round bottom flask was added 1.00 g (2.41 mmol) 2,2 bis(4-bromobenzyl)-1,3 propanediol, 0.1 g (0.5 mmol) p-toluenesulfonic acid monohydrate and 30 mL of toluene. The neck of the flask was closed with a rubber septum and the flask was purged with $N_2$. A rubber balloon/needle apparatus was filled with $N_2$ and inserted into the septum. To the mixture was added 0.34 mL (2.85 mmol) of 3,4 dimethoxythiophene and the flask was heated to 80° C. for 1 d (17 h). The flask was cooled to room temperature and the solvent was removed in vacuo. Column chromatography was performed on the residue with a silica gel column (25 cm×2.5 cm) using a gradient of pure hexanes to 30% (v/v) dichloromethane in hexanes as the eluent. 0.153 g (13%) of the desired material was obtained. IR, $^1$HNMR, $^{13}$CNMR in addition to TLC were used to confirm identity of the product.

It is important to note that the bromo-substituted derivative monomer provides a very facile route to monomers substituted with alkyl- and other substituents.

Example 6

Typical Synthesis of Monomer, 2,2-(bis-4-nitrobenzyl)-3,4-propylenedioxythiophene ("3,3-Bis(4-nitrobenzyl)-3,4-dihydro-2H-thieno[3,4-b][1,4]-dioxepine") ("Nitro-Bz-ProDOT")

a. Synthesis of the intermediate 2,2-Dimethyl-5,5-di(4-nitrobenzyl)-1,3-dioxane-4,6-dione (See Scheme, FIG. 6): An adaptation of the procedure of Fillion et al. (2005) was followed. To a 1 L round bottom flask was added 11.23 g (0.0520 mol) of 4-nitrobenzyl bromide, 3.0 g (0.0208 mol) of 2,2-dimethyl-1,3-dioxane-4,6-dione (Meldrum's acid), 9.5 g (0.0687 mol) of potassium carbonate and 150 mL of DMF. This mixture was stirred for 12 h then 700 mL of water was added to the round bottom flask. The resulting precipitate was collected and washed with water. This precipitate give was recrystallized from a methanol/dichloromethane mixture to give 7.39 g (86%). IR, $^1$HNMR, $^{13}$CNMR in addition to TLC were used to confirm identity of the product.

b. Synthesis of the intermediate 2,2-Bis(4-nitrobenzyl) malonic acid (See Scheme, FIG. 6): An adaptation of the procedure described by Tiefenbacher and Rebek (2012) was followed. To a suspension of 5.33 g (12.9 mmol) of 2,2-dimethyl-5,5-di(4-nitrobenzyl)-1,3-dioxane-4,6-dione in 60 mL of a 9:1 mixture of THF to water was added 1.11 g (46.3 mmol) LiOH. This suspension was stirred for ~17 h. After stirring, 100 mL of water was added to the suspension. The aqueous solution was washed twice with 50 mL of diethyl ether. The aqueous solution was then acidified to pH=1. The product was extracted with ethyl acetate. The ethyl acetate solution was washed once with 100 ml of water and once with 100 mL of brine. The ethyl acetate solution was dried with MgSO$_4$ and the solvent was removed in vacuo to yield 4.21 g (87%) of the desired material. IR, $^1$HNMR, $^{13}$CNMR in addition to TLC were used to confirm identity of the product.

c. Synthesis of the intermediate 2-Bis(4-nitrobenzyl)propane-1,3-diol (See Scheme, FIG. 6): An adaptation of the procedure described by Tiefenbacher and Rebek (2012) was followed. A 500 mL round bottom flask was purged with Ar and the neck of the flask was closed with a rubber septum. A rubber balloon/needle apparatus was filled with Ar and inserted into the septum. To the 500 mL round bottom flask was added 67 mL (67 mmol) of a 1.0 M solution of BH$_3$ in THF. The septum on the round bottom flask was replaced with a 125 mL addition funnel and a septum was inserted into the top of addition funnel. The whole setup was purged again with Ar and a rubber balloon/needle apparatus was filled with Ar and inserted into the septum. To the addition funnel was added 4.21 g (11.2 mmol) of 2,2-bis(4-nitrobenzyl)malonic acid in 60 mL of THF. The malonic acid solution was added to BH$_3$ solution dropwise over a period of 2 h. After the addition the entire solution was stirred for 17 h. After the stirring, 20 mL of water was added dropwise to the solution. 20 mL of a 1 M HCl was added to the solution and this mixture was stirred for 1.5 h. The product was then extracted with ethyl acetate (three times, 50 mL) and dried with MgSO$_4$. The solvent was removed in vacuo. To the resulting residue was added 50 mL of THF and 20 mL of a 1 M HCl solution. This mixture was stirred for 1.5 h. The THF was removed in vacuo and 100 mL of water was added to the residue. The product was extracted with ethyl acetate (three times, 50 mL) and dried with MgSO$_4$. Solvent was removed in vacuo to give 2.73 g (70%) of material. IR, $^1$HNMR, $^{13}$CNMR in addition to TLC were used to confirm identity of the product.

d. Synthesis of the final monomer, 2,2-(bis-4-nitrobenzyl)-3,4-propylenedioxythiophene ("3,3-Bis(4-nitrobenzyl)-3,4-dihydro-2H-thieno[3,4-b][1,4]-dioxepine") ("Nitro-Bz-ProDOT") (See Scheme, FIG. 6): To a 200 mL round bottom flask was added 2.15 g (6.21 mmol) 2,2 bis(4nitrobenzyl)-1,3 propanediol, 0.2 g (1 mmol) p-toluenesulfonic acid monohydrate and 150 mL of toluene. The neck of the flask was closed with a rubber septum and the flask was purged with N$_2$. A rubber balloon/needle apparatus was filled with N$_2$ and inserted into the septum. To the mixture was added 0.90 mL (7.55 mmol) of 3,4 dimethoxythiophene and the flask was heated to 80° C. for 1 d (17 h). The flask was cooled to room temperature and the solvent was removed in vacuo. Column chromatography was performed on the residue with a silica gel column (15 cm×2.5 cm) using a gradient of pure hexanes to 60% (v/v) dichloromethane in hexanes as the eluent. A second column (25 cm×2.5 cm) was carried out using a gradient of pure hexanes to 35% (v/v) ethyl acetate in hexanes as the eluent. 0.388 g (15%) of the desired material was obtained. IR, $^1$HNMR, $^{13}$CNMR in addition to TLC were used to confirm identity of the product.

Example 7

Typical Synthesis of Monomer, 2,2-(bis-4-aminobenzyl)-3,4-propylenedioxythiophene ("3,3-Bis(4-aminobenzyl)-3,4-dihydro-2H-thieno[3,4-b][1,4]-dioxepine") ("Amino-Bz-ProDOT")

(See Scheme, FIG. 7).
To a 200 mL round bottom flask was added 0.307 g (0.722 mmol) of 3,3-Bis(4-nitrobenzyl)-3,4-dihydro-2H-thieno[3, 4-b][1,4]-dioxepine, 2.1 g (9.3 mmol) of tin(II) chloride dihydrate and 50 mL of ethyl acetate. The solution was heated to reflux for overnight. After heating, the mixture was allowed to cool to room temperature. After cooling, 20 mL of a 0.25 M solution of sodium carbonate and 100 mL of dichloromethane were added. This mixture was vigorously stirred for 30 minutes. The mixture was then filtered through a celite pad and poured into a 500 mL separatory funnel. The organic layer was removed and washed twice with 50 mL of water and once with 50 mL of brine. The solution was dried with MgSO$_4$ and the solvent was removed in vacuo to give the product, 3,3-bis(4-aminobenzyl)-3,4-dihydro-2H-thieno [3,4-b][1,4]-dioxepine, in quantitative yield. IR, $^1$HNMR, $^{13}$CNMR in addition to TLC were used to confirm identity of the product.

Example 8

Electrochemical Deposition of the (Cathodically-Coloring) Polymer, Poly(2,2-(bis-4-chloro-benzyl)-3,4-propylenedioxythiophene) ("Poly(Cl-Bz-ProDOT)") from Monomer Solution The monomer produced as in EXAMPLE 1 was placed in a vacuum oven for about 0.5 hour before preparation of the deposition solution. Li trifluoromethane sulfonate (Li triflate) was dried in an oven at 50-55° C. overnight before use. Acetonitrile was dried using activated molecular sieves. A stock solution of 250 mL of 0.4 M Li triflate Sulf I/acetonitrile was prepared. A 4 mM solution of the Cl-BzProDOT monomer deposition solution was prepared by adding the appropriate quantity of the monomer to the 250 mL stock solution in a conical flask with stifling. A yellow deposition solution was obtained. The polymer, poly(Cl-Bz-ProDOT) was deposited on ITO/Mylar (preferred surface resistivity <60 Ohms/square, dimensionless units) using a 3 electrode configuration, with graphite counter electrode and Pt wire quasi-reference electrode. A multiple potential sweep method was used to deposit polymer, with the number of sweeps dependent on the thickness of polymer desired, which was monitored by measuring the total charge deposited using standard electrochemical methods. The optimal total charge during deposition was found to be 7.5 to 12.5 mC/cm$^2$, for films showing the best performance in devices; such films had a typical % T, at 575 nm, of 45% to 50%. A potential sweep method was found to be superior to a potentiostatic method (see COMPARATIVE EXAMPLE 9). In a typical method, potential was swept from 0 to +1.5 V (vs. Pt Q-R), at a scan rate of 10-25 mV/s, with potential step size between 2 and 7 mV. A most preferred scan rate was 12.5 to 22 mV/s and a most preferred step size 4 mV. A small difference in the scan rate, e.g. a rate of 17 mV/s vs. 13 mV/s, made a significant difference in the darkness of the films obtained and thus their suitability for the fabrication of "very dark" or "very light" devices. After deposition, the polymer film was held at an applied potential of 0.0V for 1 min, then immersed from the deposition solution while at this potential. Films were rinsed with acetonitrile, soaked in 0.2 M Li triflate/acetonitrile solution for 1 min, rinsed with acetonitrile, and dried at 50 to 75° C. Highly uniform, homogeneous polymer films with a blue/violet coloration were obtained.

Comparative Example 9

Alternative Electrochemical Deposition of the (Cathodically-Coloring) Polymer, Poly(2,2-(bis-4-chloro-benzyl)-3,4-propylenedioxythiophene) ("Poly(Cl-Bz-ProDOT)") from Monomer Solution A film of poly(Cl-Bz-ProDOT) was deposited on ITO/Mylar using a procedure identical to that of EXAMPLE 8, except that in place of the potential sweep method described, a potentiostatic (constant potential) method was used. The applied potential was held at +0.9 V in one experiment, and +1.1 V in a second, these voltages being carefully selected from the linear sweep voltammogram of the deposition solution. Total charge was carefully monitored and held close to the optimum values listed in EXAMPLE 8. The switching time of electrochromic devices made with these films was significantly slower (about 10 s vs. about 1 s) and their light/dark contrast significantly poorer (Delta % T at wavelength of maximum absorbance 30% to 50% lower), than those of EXAMPLE 8, i.e. using the potential sweep method. Additionally, some films exhibited minor cracks on drying.

Example 10

Electrochemical Deposition of the (Cathodically-Coloring) Polymer, Poly(2,2-(bis-4-bromo-benzyl)-3,4-propylenedioxythiophene) ("Poly(Br-Bz-ProDOT)", from Monomer Solution The monomer produced as in EXAMPLE 5 was used to prepare a deposition solution and then to electrochemically deposit films of the polymer, Poly(2,2-(bis-4-bromo-benzyl)-3,4-propylenedioxythiophene) ("Poly(Br-Bz-ProDOT)", on ITO/Mylar substrates. This was done in a manner substantially identical to that described in EXAMPLE 8 above, except with the following changes: (1) Monomer solution concentration used was identical (4 mM). (2) The optimal total charge during deposition was found to be 10.5 to 15.0 $mC/cm^2$, for films showing the best performance in devices; such films had a typical % T, at 575 nm, of 40% to 47%. (3) In the potential sweep method used, potential was swept from −0.3 to +1.7 V (vs. Pt Q-R), at a scan rate of 10-20 mV/s, with potential step size between 2 and 4 mV. A most preferred scan rate was 12.5 to 15 mV/s and a most preferred step size 2 mV. Highly uniform, homogeneous polymer films with a greenish-blue coloration were obtained.

Example 11

Electrochemical Deposition of the (Cathodically-Coloring) Copolymer of 2,2-(bis-4-chloro-benzyl)-3,4-propylenedioxythiophene, 2,2-(bis-4-bromo-benzyl)-3,4-propylenedioxythiophene, and 2,2-dibenzyl-3,4-propylenedioxythiophene from Monomer Solution The monomers, 2,2-(bis-4-chloro-benzyl)-3,4-propylenedioxythiophene, 2,2-(bis-4-bromo-benzyl)-3,4-propylenedioxythiophene, and 2,2-dibenzyl-3,4-propylenedioxythiophene, were used to prepare a deposition solution and then to electrochemically deposit films of the corresponding copolymer on ITO/Mylar substrates. This was done in a manner substantially identical to that described in EXAMPLE 8 above, except with the following changes: (1) The individual monomer concentrations in the deposition solution were: 2,2-(bis-4-chloro-benzyl)-3,4-propylenedioxythiophene, 0.5 mM; 2,2-(bis-4-bromo-benzyl)-3,4-propylenedioxythiophene, 0.5 mM; 2,2-dibenzyl-3,4-propylenedioxythiophene, 5 mM. (2) The optimal total charge during deposition was found to be 11 to 19 $mC/cm^2$, for films showing the best performance in devices; such films had a typical % T, at 575 nm, of 41% to 55%. (3) In the potential sweep method used, potential was swept from 0.0 to +1.7 V (vs. Pt Q-R), at a scan rate of 10-20 mV/s, with potential step size between 2 and 4 mV. A most preferred scan rate was 11 to 14 mV/s and a most preferred step size 4 mV. Highly uniform, homogeneous polymer films with a dark blue/violet coloration were obtained.

Example 12

Electrochemical Deposition of the (Anodically-Coloring) Copolymer of N,N'-Diphenyl Benzidine, Diphenyl Amine and 4-Amino-Biphenyl from Monomer Solution Preparation of the Electrodeposition (i.e., Electrochemical Polymerization) Solution: 7.5 g of the monomer N,N'-diphenyl benzidine were added to 700 mL of dry acetonitrile. The mixture was refluxed over ca. 4 h in a $N_2$ atmosphere in an appropriately sized 3-neck round bottom flask (reflux temperature approximately 83° C.). At the end of this period of reflux, 120 mL of dry N,N'-dimethyl formamide (i.e. 5.83:1 v/v % ratio, acetonitrile:DMF) were added slowly to this mixture. The temperature at first dropped slightly and then increased to ca. 87° C. Reflux was continued for ca. 2 h, the temperature remaining ca. 87° C. The entire solution was then sealed under $N_2$ and allowed to cool overnight. To this solution is added with stifling previously dried Li triflate salt in a proportion of ca. 6.24 g per 100 mL of solution. This solution may be used as is for electrochemical polymerization, if it is desired to produce the single polymer, poly(N,N'-diphenyl benzidine). If however it is desired to produce copolymers then to this solution are added, with stifling, quantities of the monomers diphenyl amine and 4-amino-biphenyl so as to obtain final concentrations of each monomer of in the ratios N,N'-diphenyl benzidine:diphenyl amine:4-amino-biphenyl of ca. 5:1:1. Previously dried Li triflate salt was added to the solution with stifling in a proportion of ca. 6.2 g per 100 mL of solution. The end result in either case is "stock solution" which is then used for all electrodepositions (i.e. electrochemical polymerizations).

Electrodeposition (Electrochemical Polymerization from Monomer Solution): The above stock solution was used for electropolymerization of the subject polymer onto ITO/Mylar substrates using a potentiostatic (i.e., constant potential) mode of deposition. A 3-electrode setup, with graphite counter and Pt wire quasi-reference electrodes was used. A potentiostatic (i.e., constant potential) deposition, at +0.5 V (vs. Pt quasi-reference) was used. Charge during deposition was monitored coulometrically, and set to between 140 and 200 $mC/cm^2$, for very light and very dark films respectively. For most preferred films yielding electrochromic devices with the best performance, a charge of 160 $mC/cm^2$ yielding a corresponding transmission at 575 nm of 69% T were most preferred. Films were immersed at an applied voltage of 0.0 V, rinsed with acetonitrile, soaked in 0.4 M Li triflate/ acetonitrile solution for 1 min, re-rinsed, and dried at ca. 60° C. for 1 hr. Highly homogeneous, uniform, green-blue films were obtained.

Comparative Example 13

Electrochemical Deposition of the (Anodically-Coloring) Polymer of N,N'-Diphenyl Benzidine, from Monomer Solution in Different Solvents Solutions of the monomer, N,N'-diphenyl benzidine (Dabs), of several concentrations ranging from 1 mM to 100 mM were prepared in N,N'-dimethyl formamide (DMF), according to the methodology described by Suzuki et al. (1989). Dry Li triflate was added to this solution to yield a concentration of 0.4 M. Electrochemical deposition (electropolymerization) of the corresponding polymer was attempted on ITO/Mylar substrates using a variety of potential step and potential sweep methods. These included the methods described by Suzuki et al. (1989), potential step methods at applied potentials (all vs. Pt quasi-reference) between +0.2 V and +1.5 V, and potential sweep methods between 0.0 V and +1.7 V (all vs. Pt quasi-reference) (cf. EXAMPLES 8, 10, 11, 12 and COMPARATIVE EXAMPLE 9). While a copious colored exudate was observed at the ITO/Mylar substrate during electro-deposition, likely indicating oligomer formation, no polymer film formation was observed on the substrate, even at times as long as 4 h. Other salts, e.g. with the above triflate anion substituted by tosylate, tetrafluoroborate and other anions, in concentrations from 0.1 M to 1 M, were also tested in the deposition solution with identical, unsuccessful results.

Electro-depositions of this monomer were also tested from acetonitrile solution, again attempting to reproduce the methodology of Suzuki et al. (1989). For this, the saturated solution of the monomer in acetonitrile, prepared as described in EXAMPLE 12, was used, with 0.4 M Li triflate added thereto. Potentiostatic deposition at potential ranging from +0.5 to +1.5 V (vs. Pt quasi-reference), and potential sweep methods as described in EXAMPLE 11, were tested. Using the potential step methods, times in excess of 2 h were required to obtain even a very thin film of the polymer (poly(N,N'-diphenyl benzidine) on the ITO substrates. Using potential sweep methods, more than 200 sweeps were required to obtain similar, very thin polymer films. Again, besides Li triflate, other salts were also tested in the deposition solution in concentrations from 0.1 M to 1 M. These results may be contrasted with those described by Suzuki et al. (1989), wherein a few potential sweeps are purportedly said to yield a thick polymer film on ITO substrates.

As described in EXAMPLE 12 above, to successfully dissolve the monomer N,N'-diphenyl benzidine in an appropriate solvent (to subsequently electro-polymerize it therefrom), it was found that an optimal solvent was DMF: acetonitrile in ca. 6:1 v/v % proportion. Several other ratios of DMF:acetonitrile were tested. It was found that, using the several different conditions of potential step, potential sweep and added salt (electrolyte) as described above, ratios of DMF:acetonitrile of 7:1 or higher were found to yield very thin polymer films over very long (>2 h) periods of deposition, whilst ratios of 5:1 or lower were found not to yield any polymer films or extremely poor films that showed very poor adhesion to the ITO substrates and could be simply shaken off in acetonitrile solvent. Thus, the ca. 6:1 ratio of DMF:acetonitrile provided an unexpectedly advantageous result in that it yielded viable films of polymer, both for the monomer N,N'-diphenyl benzidine alone, and its copolymers with other aromatic amine monomers, as described in EXAMPLE 12.

Example 14

Assembly of Dual-Polymer Electrochromic Device Comprising [Copolymer of 2,2-(bis-4-chloro-benzyl)-3,4-propylenedioxythiophene, 2,2-(bis-4-bromo-benzyl)-3,4-propylenedioxythiophene and 2,2-dibenzyl-3,4-propylenedioxythiophene] as the Cathodically Coloring Polymer and [Copolymer of N,N'-Diphenyl Benzidine, Diphenyl Amine and 4-Amino-Biphenyl] as the Anodically Coloring Polymer a. Components: An electrochemical device was fabricated substantially following the schematic depicted in FIG. 1. For "CP1", i.e. Conducting Polymer #1, the cathodically-coloring polymer, the polymer film prepared as in EXAMPLE 11 above was used. For "CP2", i.e. Conducting Polymer #2, the anodically-coloring polymer, the polymer film prepared as in EXAMPLE 12 above was used.

b. Electrolyte: A 125 mL wide-mouth conical flask was used. 3 g of Li triflate, previously dried (overnight, 60° C., vacuum oven) were added to 70 g of dry acetonitrile (ACS reagent grade, dried over molecular sieves) therein with stirring until dissolved. 7 g of poly(methyl methacrylate) (PMMA) were added very slowly (to prevent clumping) to the stirring mixture with mild heat, over 0.5 hr. Now 20 g of dry propylene carbonate (ACS reagent grade, dried over molecular sieves) were added to the mixture, now a solution, which was then allowed to sit without stifling for 1 hr. Next, a pipette for $N_2$ bubbling was introduced into the flask and slow bubbling with dry $N_2$ commenced. Slow stirring was then commenced and mild heat was applied to the flask to bring the temperature of the solution to 40° C., taking care to never exceed 50° C. This $N_2$ bubbling under stirring at ca. 40° C. was continued over a period of several hours until the volume reduced to 25 mL, yielding the final gel electrolyte as to be used in the electrochromic devices. In addition to the above described electrolyte, a large number of non-aqueous-based, prior art electrolytes, e.g. those described by Welsh et al. (1999), Sapp et al. (1998) Gazotti et al. (1998) and Groenendal et al. (2000) may be used, after suitable (and in some cases, significant) modification to accommodate the particular conducting polymer combinations used in the present invention.

c. Assembly: Devices were assembled per the schematic of FIG. 1, using the above components. The gasket used was typically of polyethylene of thickness 0.5 to 2.0 mil (ca. 13 to 50 microns). Gel electrolyte was re-warmed to ca. 30° C. for the procedure. Gaskets were set into place using the gel electrolyte as a setting glue. Electrolyte was first applied individually to the bulk of both polymer/ITO/Mylar films using a doctor blade method. Devices were then fully assembled, according to the schematic of FIG. 1. They were then clamped together using spring-loaded clamps. The clamped devices were allowed to sit overnight. Excess gel electrolyte from outer surfaces and edges was then cleaned with a Kimwipe wetted with acetonitrile. Optionally, the edges of the device could be sealed with inert, 2-component, polyurethane adhesives. For testing, electrical contact was simply made with alligator clips to the two electrodes of the devices. For a more permanent attaching of electrical lead wires, a special, commercial, space-qualified (low-outgassing) Ag epoxy was used.

Comparative Example 15

Assembly of Dual-Polymer Electrochromic Device Comprising Poly(2,2-(bis-4-chloro-benzyl)-3,4-propylenedioxythiophene) ("Poly(Cl-Bz-ProDOT)") as the Cathodically Coloring Polymer and [Copolymer of N,N'-Diphenyl Benzidine, Diphenyl Amine and 4-Amino-Biphenyl] as the Anodically Coloring Polymer An electrochemical device was fabricated substantially as described in EXAMPLE 14 except that, in place of the cathodically coloring polymer in that EXAMPLE, which was a copolymer constituted from three separate monomers, the simple polymer, poly(2,2-(bis-4-chloro-benzyl)-3,4-propylenedioxythiophene) ("poly(Cl-Bz-ProDOT)") was used. In particular, it was ensured the polymer thicknesses, as measured by the total amount of charge deposited, was nearly identical to those for the corresponding polymers in EXAMPLE 14.

Comparative Example 16

Assembly of Dual-Polymer Electrochromic Device Comprising [Poly(isothianaphthene) (PITN)] as the Cathodically Coloring Polymer and [Copolymer of N,N'-Diphenyl Benzidine, Diphenyl Amine and 4-Amino-Biphenyl] as the Anodically Coloring Polymer An electrochemical device was fabricated substantially as described in EXAMPLE 14 except that, in place of the cathodically coloring polymer in that EXAMPLE, poly (isothianaphthene) (PITN) was used. A PITN film was electrochemically polymerized on ITO/Mylar as described by Chandrasekhar et al. (1989). In particular, it was ensured the thickness of the anodically coloring copolymer, as measured by the total amount of charge deposited, was nearly identical to that for the anodically coloring copolymer of EXAMPLE 14.

Comparative Example 17

Assembly of Single-Polymer Electrochromic Device Comprising Poly(N,N'-Diphenyl Benzidine) as the Anodically Coloring Polymer An electrochemical device was fabricated substantially as described in EXAMPLE 14 except that, in place of the cathodically coloring polymer in that EXAMPLE, no cathodically coloring polymer, i.e. a blank ITO/Mylar electrode, was used.

Example 18

Characterization of Electrochromic Devices

Devices as assembled in EXAMPLE 14 and COMPARATIVE EXAMPLES 15-17 were characterized via cyclic voltammetry (in 2-electrode mode) and spectroscopically. The latter was carried out using a PC-controlled Perkin-Elmer Lambda 12 double-beam spectrometer, with nothing (i.e., air) in the reference compartment; this may be contrasted with most of the published literature and patent data, which use a "blank" substrate or device, i.e. one of identical construction to the polymer device except that it does not have any active electrochromic material, as reference. UV-Vis-NIR spectra were taken while the device was held potentiostatically at appropriate potentials corresponding to its extreme light and dark states. For monitoring the switching time, the spectrometer was brought to the wavelength of maximum absorption of the devices (575 nm for the device of EXAMPLE 14) and the device then rapidly switched between its extreme light and dark state with appropriate applied voltage. Relevant results are presented in the FIGURES.

Comparative Example 19

Long Term/Lifetime Testing of Electrochromic Devices Fabricated Gel Electrolyte Testing (as per procedure of EXAMPLE 18) of electrochromic devices fabricated as described in Example 14

Three devices were fabricated (per EXAMPLE 14) and tested for electrochromic performance per the procedures described in EXAMPLE 18 above. They were left on the shelf and re-tested after a period of 23 months. Their electrochromic performance, measured in terms of the light and dark state UV-Vis-NIR spectra and switching time, was found to have changed less than 2.5%. In particular, the light/dark contrast, measured in units of Delta % T at any particular wavelength, was found to have degraded less than 2% for two of the devices and to actually have increased by 1.5% for the third device. Light/dark switching times, measured at 575 nm, were found to have increased less than 2.5%. Peaks of the cyclic voltammograms of the devices before and after this 23 month period were very similar, with mA-scale peaks in all cases.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of patent and non-patent publications are cited in the specification in order to describe the state of the art to which this invention pertains. The entire disclosure of each of these publications is incorporated by reference herein.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All electrochromic devices, compositions and methods for preparing the same that embody the present invention can, in alternate embodiments, be more specifically defined by any of the transitional terms "comprising", "consisting essentially of" and "consisting of".

REFERENCES (1) Lee, S.-H.; Tracy, E.; Pitts, R.; Jorgensen, G. J., "Electrochromic Counter Electrode" U.S. Pat. No. 6,859,297 (2005).
(2) Chandrasekhar, P., "Electrochromic Display Device", U.S. Pat. No. 5,995,273 (1999).
(3) Chandrasekhar, P., "Electrolytes", U.S. Pat. No. 6,033,592 (2000).
(4) Suzuki, T.; Yoshikawa, M.; Kojima, A., "N,N'-Diphenylbenzidine Polymer and Method of producing The Same" U.S. Pat. No. 4,874,481 (1989).
(5) Chandrasekhar, P.; Masulaitis, A. M.; Gumbs, R. W., "Novel Synthesis, Spectroelectrochemical, Electrochemical and Chronovoltabsorptometric Characterization of Poly(Isothianaphthene)" *Synth. Met.*, (1990), 36 (3), 303-326.
(6) Chandrasekhar, P.; Gumbs, R. W., "Novel Synthesis, Spectroelectrochemical, Electrochemical and Chronovoltabsorptometric Characterization of Family of Poly-(Aromatic Amines), Novel Processible Conducting Polymers. I. Poly(benzidines)", *J. Electrochem. Soc.*, (1991), 138, 1337-1346.
(7) Chandrasekhar, P.; Thorne, J. R. G., Hochstrasser, R. M., "Third-order Nonlinear Optical Properties of Poly (diphenyl Amine) and Poly(4-Amino Biphenyl), Novel Processible Conducting Polymers", *Appl. Phys. Lett.*, (1991), 59, 1661-3.
(8) (Non-edited textbook): Chandrasekhar, P. *Conducting Polymers: Fundamentals and Applications. A Practical Approach*, with foreword by Lawrence Dalton: Kluwer Academic Publishers (now Springer Verlag), Dordrecht, The Netherlands and Norwell, Mass., USA, ISBN No. 0-7923-8564-0 (August 1999).
(9) Gazotti, W. A.; Casalbore-Miceli, G.; Geri, A.; De Paoli, M.-A., "A Solid-State Electrochromic Device Based on Two Optically Complementary Conducting Polymers", *Adv. Mat.*, 10, 60-64 (1998).
(10) Krishnamoorthy, K.; Ambade, A. V.; Kanungo, M.; Contractor, A. Q.; Kumar, A., "Rational design of an electrochromic polymer with high contrast in the visible region: dibenzyl substituted poly(3,4-propylenedioxythiohene)", *J. Mat. Chem.* 11, 2909-2911 (2001).
(11) Welsh, D. M.; Kumar, A.; Meijer, E. W.; Reynolds, J. R., "Enhanced Contrast Ratios and Rapid Switching in Electrochromics Based on Poly(3,4-propylenedioxythiophene) Derivatives", *Adv. Mat.* 11, 1379-1382 (1999).
(12) Sapp, S. A.; Sotzing, G. A.; Reynolds, J. R., "High Contrast Ratio and Fast -Switching Dual Polymer Electrochromic Devices", *Chem. Mater.*, 10, 2101-2108 (1998).
(13) Groenendaal, L.; Jonas, F.; Freitag, D.; Pielartzik, H.; Reynolds, J. R., "Poly(3,4-ethylenedioxythiophene) and Its Derivatives: Past, Present and Future", *Adv. Mat.*, 12, 481-494 (2000).
(14) Chandrasekhar, P.; Zay, B. J.; Birur, G. C.; Rawal, S.; Pierson, E. A.; Kauder, L.; Swanson, T., "Polymers with Large, Dynamic Electrochromism in the Mid- and Far-infrared", *Advanced Functional Materials*, 12 (2), 95-103 (2002).
(15) Chandrasekhar, P.; Wheeler, R. A.; Hoffmann, Roald, "Sigma Bond Cleavage in Coordinated Dioxygen: The Case of the u-Peroxo Complex [(THF)$_3$Cl$_2$V(III)(O$_2{}^{2-}$)-V(III)Cl$_2$(THF)$_3$] and Vanadyl Formation in Solution", *Inorg. Chim. Acta*, (1987), 59, 386.
(16) Guay, J.; Dao, L. H., "Formation of poly(-phenylaniline) by electropolymerization of 4-aminobiphenyl or diphenylamine", *J. Electroanal. Chem.*, 274, 135-142 (1989).
(17) Nguyen, M. T.; Dao, L. H., "Synthesis, characterization and properties of poly -(3-methyldiphenylamine) and poly(3-methoxydiphenylamine)", *J. Electroanal. Chem. Interfac. Electrochem.*, 289, 37-53 (1990).
(18) Guay, J.; Leclerc, M.; Dao, L. H., "Conducting polymer derived from 4-aminobiphenyl" *J. Electroanal. Chem. Interfac. Electrochem.*, 251, 31-39 (1988).
(19) Leclerc, M.; Guay, J.; Dao, L. H., "Synthesis and properties of electrochromic polymers from toluidines", *J. Electroanal. Chem. Interfac. Electrochem.*, 251, 21-29 (1988).
(20) Nguyen, M. T.; Dao, L. H., "Electrochemical, electrochromic, and conductive properties of poly(N-alkyldiphenylamine) polymers", *J. Chem. Soc., Chem. Commun.*, 1221-1222 (1990).
(21) Hotta, S.; Rughooputh, S. D. D. V.; Heeger, A. J.; Wudl, F., Macromolecules, 20, 212 (1987).
(22) Patil, A. O.; Ikenoue, Y.; Wudl, F.; Heeger A. J., *J. Am. Chem. Soc.*, 109, 1858 (1987).
(23) Ram, M. K.; Maccioni, E.; Nicolini, C., "The electrochromic response of polyaniline and its copolymeric systems", *Thin Solid Films*, 303, 27-33 (1997).
(24) Menon, R.; Yoon, C. O.; Moses, D; Heeger, A. J., "Metal-Insulator Transition in Doped Conducting Polymers", in *Handbook of Conducting Polymers*, 2nd Edition, pg. 27, Ed by Skotheim, T. A.; Reynolds, J. (Eds.), CRC Press, Boca Rato, Fla., USA, (1998).
(25) Fillion, E.; Fishlock, D.; Wilsily, A.; Goll, J. M. *J. Org. Chem.* 2005, 70, 1316.
(26) Tiefenbacher, K.; Rebek, Jr., *J. Am. Chem. Soc.* 2012, 134, 2914.
(27) Invernale, M. A.; Seshadri, V.; Mamangun, D. M. D.; Ding, Y.; Filloramo, J; and Sotzing, G. A. *Chem. Mater.* 2009, 21, 3332-3336.
(28) Padilla, J; Seshadri, V.; Filloramo, J.; Mino, W. K.; Mishra, S. P.; Radmard, B.; Kumar, A.; Sotzing, G. A.; and Otero, T. F. *Synthetic Metals* 2007, 157, 261-268.

I claim:

1. A method for preparing an electrode, wherein the electrode comprises a polymer comprising N,N'-diphenyl benzidine monomer, the method comprising the steps of:
   (a) providing a deposition solution comprising the N,N'-diphenyl benzidine monomer;
   (b) uniformly depositing the polymer onto a substrate in contact with the deposition solution to yield the electrode; and
   wherein the deposition solution comprises dimethylformamide and acetonitrile in a ratio of at least about 6:1 by volume, respectively.

2. The method of claim 1, wherein the deposition solution further comprises one or more of diphenyl amine monomer and 4-aminobiphenyl monomer.

3. The method of claim 1, wherein the deposition solution comprises N,N'-diphenyl benzidine monomer, diphenyl amine monomer, and 4-aminobiphenyl monomer in a molar ratio in the range of about 1:1:1: to 50:1:1, respectively.

4. The method of claim 1, wherein the deposition solution comprises N,N'-diphenyl benzidine monomer, diphenyl amine monomer, and 4-aminobiphenyl monomer in a molar ratio in the range of about 1:1:1: to 20:1:1, respectively.

5. The method of claim 1, wherein the deposition solution comprises N,N'-diphenyl benzidine monomer, diphenyl amine monomer, and 4-aminobiphenyl monomer in a molar ratio in the range of about 1:1:1: to 9:1:1, respectively.

6. The method of claim 1, wherein the deposition solution comprises N,N'-diphenyl benzidine monomer, diphenyl amine monomer, and 4-aminobiphenyl monomer in a molar ratio in the range of about 3:1:1: to 7:1:1, respectively.

7. The method of claim 1, wherein the deposition solution comprises N,N'-diphenyl benzidine monomer, diphenyl amine monomer, and 4-aminobiphenyl monomer in a molar ratio of about 5:1:1, respectively.

8. The method of claim 1, wherein the deposition solution comprises a salt.

9. The method of claim 8, wherein the salt comprises one or more of lithium triflate and $LiBF_4$.

10. The method of claim 1, wherein the substrate comprises a conductive transparent substrate.

11. The method of claim 10, wherein the conductive transparent substrate comprises one or more of an indium-tin-oxide(ITO)/glass substrate, ITO/poly(ethylene terephthalate) (PET) substrate, tin-oxide/glass substrate, tin-oxide/PET substrate, gold/glass substrate, carbon-nanotubes/glass substrate, carbon-nanotubes/PET substrate, and gold/PET substrate.

* * * * *